US011896854B2

(12) United States Patent
Scheiner

(10) Patent No.: US 11,896,854 B2
(45) Date of Patent: *Feb. 13, 2024

(54) HYGIENE MASK WITH SEAL FORMING STRUCTURE

(71) Applicant: ResMed Pty Ltd, Bella Vista (AU)

(72) Inventor: Rupert Christian Scheiner, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 57 days.

This patent is subject to a terminal disclaimer.

(21) Appl. No.: 17/529,375

(22) Filed: Nov. 18, 2021

(65) Prior Publication Data

US 2022/0072344 A1     Mar. 10, 2022

Related U.S. Application Data

(63) Continuation of application No. 17/161,846, filed on Jan. 29, 2021, now Pat. No. 11,213,702.

(30) Foreign Application Priority Data

Aug. 31, 2020   (AU) ................. 2020903106

(51) Int. Cl.
*A62B 18/02* (2006.01)
*A62B 18/08* (2006.01)
(Continued)

(52) U.S. Cl.
CPC ........ *A62B 18/025* (2013.01); *A41D 13/1161* (2013.01); *A61M 16/0605* (2014.02);
(Continued)

(58) Field of Classification Search
CPC ....... A62B 18/02; A62B 18/025; A62B 18/08; A62B 18/084; A62B 23/00; A62B 23/02;
(Continued)

(56) References Cited

U.S. PATENT DOCUMENTS 2,237,305 A   4/1941 Heimann
2,296,150 A   9/1942 Dockson et al.
(Continued)

FOREIGN PATENT DOCUMENTS

CN   204048143 U   12/2014
CN   104489967 A   4/2015
(Continued)

OTHER PUBLICATIONS

Innovation in Textiles: "Baltex pivots to manufacture Airox AX100 textile face masks" https://www.innovationintextiles.com/baltex-pivots-to-manufacture-airox-ax100-textile-face-masks/ (Year: 2020).*

(Continued)

*Primary Examiner* — Valerie L Woodward
*Assistant Examiner* — Paige Kathleen Bugg
(74) *Attorney, Agent, or Firm* — Nixon & Vanderhye P.C.

(57) ABSTRACT

A mask for use at an operating pressure substantially equal to atmospheric pressure includes a body with a three-dimensional shaped chamber that is configured to receive a user's mouth and nares and operate at the operating pressure. The mask also includes a nose portion having an uppermost portion sized to avoid contact with the user's nasal ridge and to contact the user's nose along the user's sagittal plane and around at least a portion of the user's nares on an inferior side of the user's nose inferior to the user's nasal ridge. The nose portion is constructed from an at least partially impermeable material to limit airflow toward the user's eyes in use. The mask also includes a positioning and stabilising structure to provide a force to hold the seal forming structure in position against the user.

27 Claims, 24 Drawing Sheets

(51) Int. Cl.
*A62B 23/02* (2006.01)
*A62B 7/10* (2006.01)
*A41D 13/11* (2006.01)
*A61M 16/06* (2006.01)

(52) U.S. Cl.
CPC ........... *A61M 16/0683* (2013.01); *A62B 7/10* (2013.01); *A62B 18/08* (2013.01); *A62B 18/084* (2013.01); *A62B 23/025* (2013.01)

(58) Field of Classification Search
CPC ......... A62B 23/025; A62B 23/06; A62B 7/10; A41D 13/11; A41D 13/1107; A41D 13/1115; A41D 13/1123; A41D 13/113; A41D 13/1138; A41D 13/1161; A41D 13/1169; A41D 13/1176; A61M 16/00; A61M 16/06; A61M 16/0605; A61M 16/0611; A61M 16/0622; A61M 16/0683; A61M 16/0688
See application file for complete search history.

(56) References Cited

U.S. PATENT DOCUMENTS

| | | | |
|---|---|---|---|
| 4,671,271 A | 6/1987 | Bishop et al. | |
| 4,782,832 A | 11/1988 | Trimble et al. | |
| 4,944,310 A | 7/1990 | Sullivan | |
| 5,687,715 A | 11/1997 | Landis | |
| 6,532,959 B1 | 3/2003 | Berthon-Jones | |
| 6,575,165 B1* | 6/2003 | Cook | A62B 9/006 128/205.27 |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,643,048 B1* | 5/2017 | Danford | A63B 21/00069 |
| 10,322,312 B1 | 6/2019 | Danford | |
| 11,213,702 B1* | 1/2022 | Scheiner | A62B 18/084 |
| 2004/0089303 A1 | 5/2004 | Chien | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2012/0017911 A1 | 1/2012 | Choi | |
| 2014/0190492 A1* | 7/2014 | Noh | A41D 13/1138 128/863 |
| 2014/0326245 A1* | 11/2014 | Teng | A41D 13/1115 128/206.13 |
| 2015/0352382 A1* | 12/2015 | Jayaraman | A62B 18/02 128/206.13 |
| 2016/0082214 A1 | 3/2016 | Barlow | |
| 2016/0296720 A1 | 10/2016 | Henry | |
| 2017/0000964 A1 | 1/2017 | Shafer | |
| 2017/0128689 A1* | 5/2017 | Law | A61M 16/0683 |
| 2017/0172137 A1 | 6/2017 | Wynalda | |
| 2018/0125700 A1 | 5/2018 | Ray | |
| 2018/0169367 A1* | 6/2018 | Chodkowski | A61M 16/0622 |
| 2018/0256845 A1* | 9/2018 | Gibson | A61M 16/0683 |
| 2018/0264218 A1 | 9/2018 | Chodkowski | |
| 2018/0280738 A1* | 10/2018 | Gabriel | A62B 18/025 |
| 2018/0318539 A1* | 11/2018 | Scheiner | A61M 16/06 |
| 2020/0016356 A1 | 1/2020 | Patel | |
| 2020/0108218 A1* | 4/2020 | Bock-Aronson | A62B 18/025 |
| 2020/0121005 A1* | 4/2020 | Belousov | A41D 13/1107 |
| 2021/0316173 A1 | 10/2021 | Elsherif | |
| 2022/0072344 A1 | 3/2022 | Scheiner | |

FOREIGN PATENT DOCUMENTS

| | | |
|---|---|---|
| CN | 205250408 U | 5/2016 |
| CN | 106617384 A | 5/2017 |
| CN | 207054886 U | 3/2018 |
| CN | 110250617 A | 9/2019 |
| CN | 111358084 A | 7/2020 |
| DE | 202011106611 U1 | 11/2011 |
| GB | 2385533 A | 8/2003 |
| KR | 20170015033 A | 2/2017 |
| KR | 20170101109 A | 9/2017 |
| KR | 102127942 B1 | 6/2020 |
| KR | 20200067779 A | 6/2020 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | 2017/114585 A1 | 7/2017 |
| WO | 2017/120643 A1 | 7/2017 |
| WO | WO-2019183680 A1 * | 10/2019 ........ A61M 16/0605 |

OTHER PUBLICATIONS

"*Respiratory Physiology*", by John B. West, Lippincott Williams & Wilkins, 9$^{th}$ edition published 2012 (8 pages).
Written Opinion of the International Preliminary Examining Authority dated Aug. 3, 2022 issued in International Application No. PCT/AU2021/051006 (4 pages).
International Search Report dated Nov. 10, 2021 issued in PCT/AU2021/051006 (5 pages).
Written Opinion of the International Searching Authority dated Nov. 10, 2021 issued in PCT/AU2021/051006 (5 pages).
Office Action dated Aug. 2, 2023 issued in U.S. Appl. No. 18/023,550 (82 pages).

* cited by examiner

HYGIENE MASK WITH SEAL FORMING STRUCTURE

CROSS-REFERENCE TO RELATED APPLICATIONS

This application is a continuation of U.S. application Ser. No. 17/161,846, filed Jan. 29, 2021, now allowed, which claims the benefit of Australian Provisional Application No. 2020903106, filed Aug. 31, 2020, the entire contents of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

BACKGROUND OF THE TECHNOLOGY

Field of the Technology

The present technology relates to masks or user interfaces, and in particular, but not exclusively, to hygiene masks.

Description of Related Art

The respiratory system of the body facilitates gas exchange. The nose and mouth form the entrance to the airways of a person.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

Particles in the air travel into a person's airways when they inhale. These particles can include dirt, bacteria, viruses, or other debris that can harm the person. Similarly, people exhale particles (e.g., droplets, aerosols, etc.). These particles can contain bacteria, viruses, or other debris that can harm other people who eventually inhale (or otherwise come in contact with) the particles.

People can wear masks to block particles from entering their airways and/or to block particles from exiting their airways. These masks can be referred to as hygiene masks.

Hygiene masks, for example those worn by medical practitioners (e.g. during surgery) may suffer from a number of disadvantages. Known hygiene masks typically have a periphery which extends over the user's nose (e.g. sometimes over the ridge and/or bridge of the nose), across the cheek (e.g. close to or across the zygomatic bones) and under the chin. Typically, such masks do not conform well to the profile of the user's face around the area of the nose and cheek, and one or more spaces are created between the periphery of the mask and the surface of the user's face. This may be more pronounced when the user is moving parts of their face (e.g., when talking). When the user exhales, a portion of the exhaled air escapes through this space. This can result in the user experiencing dry eyes. Then exhaled air directed toward the user's eyes is particularly inconvenient if the user is wearing glasses (e.g., prescription glasses, sunglasses, safety glasses, etc.), as the exhaled breath may cause fogging of their glasses.

Some existing hygiene masks attempt to minimise this issue by providing a malleable metal component at a superior portion of the mask (e.g., the portion configured to contact the ridge of the user's nose). The malleable metal component can be deformed by the user to conform to the shape of their nasal ridge. However, this solution is typically only partially successful, and the space or gap referred to above is usually present to some extent. In other words, although the amount of exhale air directed toward the user's eyes may be lessened, the user may still experience dry eyes and/or the fogging of glasses.

Hygiene masks which extend over the user's nose ridge may suffer from other limitations. Many such masks may be bulky and may reduce the user's field of vision below the horizontal. Some potential users may also be put off by the size of conventional masks and may therefore avoid using them. In some other circumstances, a mask with a large footprint on the face results in a volume of warm air being trapped between the mask and the user's face due to the exhaled breath being of a certain temperature and humidity.

It is an aspect of the present technology to provide a mask which overcomes or ameliorates at least one problem with the masks of the prior art.

Alternatively, it is an aspect of the present technology to at least provide the public with a useful choice.

BRIEF SUMMARY OF THE TECHNOLOGY

The present technology is directed towards providing medical devices used to limit the spread of airborne particles having one or more of improved comfort, cost, efficacy, ease of use, and manufacturability.

A first aspect of the technology relates to an apparatus used in limiting the spread of airborne particles by limiting particles inhaled into a user's airways, and by limiting particles exhaled into the environment.

Another aspect of the technology relates to methods used in limiting the spread of airborne particles by limiting particles inhaled into a user's airways, and by limiting particles exhaled into the environment.

One form of the present technology comprises a hygiene mask which forms a seal around the user's nares.

One form of the present technology comprises a hygiene mask which forms a seal with anterior and lateral portions of a periphery of the alar base of a user's nose.

Another form of the present technology comprises a mask comprising a foam or textile body and seal forming structure which is constructed from foam.

Another form of the present technology comprises a hygiene mask which does not touch the user's nose above the greater alar cartilage and which does not extend below the user's chin.

One form of the present technology comprises a mask comprising:

a body configured to surround a user's nares and the user's mouth; and a positioning and stabilizing structure to provide a force to hold the body in position on the user's head.

Another form of the present technology comprises a hygiene mask comprises a body that forms a chamber that is configured to receive a user's mouth and nares at substantially atmospheric pressure.

Another form of the present technology comprises a hygiene mask configured to filter inhaled and exhaled air, and direct exhale air away from the user's eyes.

Another form of the present technology comprises a hygiene mask configured to seal against a user's face and limit airflow from leaking out of a chamber of the mask.

Another form of the present technology comprises a mask configured to seal against a user's face and prevent airflow between the outer perimeter of the mask and user's skin, the mask including a permeable body configured to allow inhaled and exhaled air to pass through.

Another form of the present technology comprises a mask comprising:

a body;

a seal forming structure connected to the body, the seal forming structure configured to form a seal around the user's mouth and around the user's nares; and a positioning and stabilizing structure to provide a force to hold the seal forming structure in position on the user's head.

Another form of the present technology comprises a mask comprising:

a body defining a chamber; and a seal forming structure comprising a cantilever structure extending, in use, from the body toward a user's face, the cantilever structure configured to form a seal around an inferior periphery of the user's nose, the seal forming structure further configured to form a seal around the user's mouth, wherein at least a portion of the body is configured to allow passage of air into and out of the chamber, the mask further comprising a positioning and stabilising structure to provide a force to hold the seal-forming structure in position on the user's head.

In examples:
a) the body comprises a port through which air can enter and exit the chamber;
b) at least a portion of the body is porous, such that air can enter and exit the chamber;
c) the seal forming structure comprises a portion configured to at least partially seal on the user's face between the chin and the lip inferior;
d) the cantilever structure seals to user's face directly inferior the alar crest;
e) the cantilever structure seals to the user's face above the lip superior;
f) the seal forming structure does not form a seal superior to the lip superior directly inferior to the user's subnasale and nares;
g) a portion of the cantilever structure extends around 20 mm from the body;
h) the body is formed from a spacer fabric;
i) the body forms a cupped shape;
j) the body is formed from at least one flat sheet;
k) the body comprises at least one pleat.
l) the body is formed from a thermoformed material;
m) a central superior portion of a perimeter of the body is provided with a plastically deformable element;
n) the mask is provided with at least one replaceable filter element;
o) the at least one filter element is provided to an interior of chamber;
p) the at least one filter element covers substantially an entire interior surface of the body;
q) the position and stabilising structure comprises two elastic loops, each loop configured to engage one of the user's ears;
r) the elastic loops are connected to the body around at least a majority of perimeter of body;
s) the elastic loops are connected to the body around substantially the entire perimeter of the body; and/or
t) the positioning and stabilising structure comprises at least one strap which passes around the back of the user's head.

Another form of the technology comprises a mask for use at an operating pressure substantially equal to atmospheric pressure, the mask comprising:

a body defining a chamber configured to operate at the operating pressure throughout the user's respiratory cycle and configured to receive a user's mouth and nares; and a seal forming structure configured to form a seal against the user's face in use, the seal forming structure comprising:

a nose seal portion configured to extend around at least a portion of the user's nares on an inferior side of the user's nose, the nose seal portion including a cantilever structure extending from the body toward the user's face in use, the cantilever structure configured to form a seal around anterior and lateral portions of a periphery of the alar base of the user's nose, and a mouth seal portion configured to form a seal at least partially around the user's mouth, wherein an end of the nose seal portion is directly connected to an end of the mouth seal portion; and a positioning and stabilising structure to provide a force to hold the seal forming structure in position on the user's head wherein at least a portion of the body is configured to allow passage of air into and out of the chamber.

In some examples: a) the body comprises a port through which air can enter and exit the chamber; b) the body is substantially impermeable and air can only enter and exit the chamber through the port, in use; c) at least a portion of the body is permeable, such that air can enter and exit the chamber through a surface of the body; and/or d) the mouth seal portion is configured to seal on the user's face between the chin and the lip inferior.

In some examples: a) the cantilever structure seals to user's face directly inferior of the alar crest; b) the cantilever structure seals to the user's face above the lip superior; c) the seal forming structure does not form a seal above the user's lip superior directly inferior to the user's subnasale and nares; and/or d) a portion of the cantilever structure extends around 20 mm from the body.

In some examples: a) the body is formed from a spacer fabric, a foam, and/or a thermoformed material; b) the body forms a cupped shape with an inner surface of the body having a substantially positive domed shape with respect to the user, in use; c) the body is formed form a rigid or semi-rigid material; d) the body maintains its cupped shaped regardless of whether the user has donned the mask; e) the body is formed from a flat sheet and comprises at least one pleat; f) the cantilever structure is connected to the body using an adhesive, sewing, and/or ultrasonic welding; g) a central superior portion of a perimeter of the body is provided with a plastically deformable element; and/or h) the plastically deformable element is constructed from metal.

In some examples: a) at least one filter element configured to filter air prior to entering and/or exiting the chamber; b) the at least one filter element is provided to an interior surface of chamber; c) the at least one filter element covers substantially an entire interior surface of the body; d) the interior surface includes at least one fastener; e) the filter element is configured to removably connected to the at least one fastener; f) the at least one fastener is formed from a hook and loop material; g) a rigid member is coupled to at least a portion of an outer perimeter of the filter element; and/or h) the rigid member is resilient and configured to return to a neutral position after a compressive force is removed.

In some examples: a) the position and stabilising structure comprises two elastic loops, each loop configured to engage one of the user's ears; b) the elastic loops are connected to the body around at least a majority of perimeter of body; and/or c) the elastic loops are connected to the body around substantially an entire perimeter of the body.

In some examples: a) the nose seal portion is configured to not extend into the user's nares; b) the nose seal portion and the mouth seal potion are configured to cooperate to form a single, continuous seal against the user's face, in use; c) the nose seal portion is constructed from a single piece of material; d) the nose seal portion is symmetric about a central portion configured to contact the user's nose proximate to the pronasale, in use; e) the cantilever structure includes an anterior edge that is at least partially linear; and/or f) the positioning and stabilising structure is connected to the body in a parallel orientation with the anterior edge.

In some examples: a) the body includes an outer surface, and inner surface, and an edge between the outer surface and the inner surface; b) the positioning and stabilising structure is connected to the edge; c) the positioning and stabilising structure is connected to the edge with an adhesive; d) the positioning and stabilising structure includes an upper arm and a lower arm each connected to the edge; and/or e) the upper arm and the lower arm are oriented substantially tangential from a central portion of the nose seal portion.

In some examples: a) the nose seal portion includes an anterior edge and a posterior edge configured to contact the user's face; b) a maximum width between the anterior edge and the posterior edge is configured to contact the user proximate to the alar base; c) a lateral edge of the nose seal portion includes a minimum width between the anterior edge and the posterior edge, the lateral edge connected to the mouth seal portion; d) the posterior edge proximate to the maximum width is arcuate; and/or e) the minimum width between the anterior edge and the posterior edge is substantially equal to a thickness of the mouth seal portion.

Another form of the present technology comprises a hygiene mask configured to filter the air a user inhales, the hygiene mask comprising:

a body having a three-dimensional shape in order to form a chamber;

a seal forming structure configured to seal against the user's face in use; and a positioning and stabilising structure connected to the body, the positioning and stabilising structure configured to provide a force to hold the seal forming structure in position on the user's head.

In some examples: a) the seal forming structure is configured to direct air through the body and away from the user's eyes; b) the seal forming structure forms a single seal around the user's mouth and nares; c) the seal forming structure includes a nose seal portion constructed from a first piece of material, and a mouth seal portion constructed from a second piece of material; d) the nose seal portion is configured to not extend within the user's nares; e) the nose seal portion includes an anterior edge connected to the body, a posterior edge opposite the anterior edge, and a superior surface extending between the posterior edge and the anterior edge; f) the user's face configured to contact the posterior edge and the superior surface; g) the posterior edge includes a substantially circular shape at a maximum width between the anterior edge and the posterior edge; h) the superior surface proximate to the maximum width is configured to contact the user's face at or adjacent to the alar base; i) the nose seal portion is curved about two axes; j) a width between the anterior edge and the posterior edge tapers toward a lateral end of the nose seal portion, and the width at the lateral end configured to equal a thickness of the mouth seal portion; k) the seal forming structure is connected to the body proximate to an outer perimeter of the body; and/or l) the seal forming structure is constructed from a textile material and/or a foam material.

In some examples: a) the body is constructed from a rigid or semi-rigid material and is configured to maintain its three-dimensional shape; b) the body has a substantially cupped shape, and forms a positively domed shape with respect to a user in use; c) a deformable element is coupled to an inner surface of the body proximate to an outer perimeter of the body; d) the deformable element is plastically deformable and is configured to maintain its shape; e) the deformable element is metal; f) the inner surface of the body is configured to be spaced apart from the user's mouth in use; g) the inner surface of the body includes a fastener configured to removably couple to a filter element; h) the body is constructed with a pleat so that there are substantially no folds along the surface of the body; and/or i) the chamber of the body is substantially maintained at the operating pressure in use.

In some examples: a) the material used to construct the body is permeable and is configured to allow airflow into and out of the chamber through the body; b) the material used to construct the body may be cellulose acetate, cellulose nitrate (e.g., collodion), polyamide (e.g., nylon), polycarbonate, polypropylene, and/or polytetrafluoroethylene (e.g., Teflon); c) the body is constructed from a textile and/or a foam material; and/or d) the body is constructed from a spacer fabric.

In some examples: a) the body includes a port through which air can enter and exit the chamber; b) the body is constructed from an impermeable material and/or is coated with an impermeable material; c) a filter is positioned within the port and is configured to filter particles out of the inhaled and/or exhaled air; and/or d) the filter is removable from the port.

In some examples: a) the positioning and stabilising structure is configured to extend around the user's ears; b) the positioning and stabilising structure includes a pair of loops that are each configured to engage one of the user's ears; c) each loop of the pair of loops is constructed from an elastic material and is configured to stretch to fit different sized user's; and/or d) the loop forms a continuous perimeter.

In some examples: a) the positioning and stabilising structure includes a pair of upper straps and a pair of lower straps; b) a left upper strap is configured to connect to a right upper strap in use; c) a left upper strap is configured to connect to a left lower strap in use; d) a left lower strap is configured to connect to a right lower strap in use; e) a right lower strap is configured to connect to a right upper strap in use; f) the straps are connected together using magnets, knots, snaps, hook and loop material, adhesives, buckles, and/or any other similar fastener; and/or g) the upper and lower straps are flexible and substantially inextensible.

In some examples: a) a filter element is connected to the body to filter air flowing into and out of the chamber; b) the filter is removably coupled to the body; c) the filter element is coupled to an inner surface of the body; d) the filter element is configured to engage a fastener on an inner surface of the body; e) the filter element overlays substantially the entire inner surface; f) the filter element is cleanable and reusable; and/or g) the filter element is replaceable.

Another example of the present technology comprises a mask for use at an operating pressure substantially equal to atmospheric pressure, the mask comprising:

a body forming a three-dimensional shaped chamber configured to operate at the operating pressure and configured to receive a user's mouth and nares, wherein an inner surface of the body has a substantially positive domed shape with respect to the user, in use throughout the user's respiratory cycle; and a seal forming structure configured to form a seal against the user's face in use, the seal forming structure comprising:

a nose seal portion configured to extend around at least a portion of the user's nares on an inferior side of the user's nose, the nose seal portion including a cantilever structure extending from the body toward the user's face in use, the cantilever structure configured to form a seal around anterior and lateral portions of a periphery of the alar base of the user's nose, the cantilever structure including a central portion configured to contact an inferior region of the user's nose proximate to the user's pronasale, a pair of lateral end portions configured to contact the user proximate the nasolabial sulcus, and a pair of middle portions, each middle portion of the pair of middle portions between the central portion and one lateral end portion of the pair of lateral end portions, each middle portion configured to contact the user's face proximate to the alar base, and a mouth seal portion configured to form a seal at least partially around the user's mouth and between the chin and the lip inferior, the mouth seal connected to the pair of lateral ends to form a single, continuous seal, wherein an end of the nose seal portion is directly connected to an end of the mouth seal portion; and a positioning and stabilising structure to provide a force to hold the seal forming structure in position on the user's head;

wherein at least a portion of the body is configured to allow passage of air into and out of the chamber.

Another example of the present technology comprises a mask for use at an operating pressure substantially equal to atmospheric pressure, the mask comprising:

a body forming a three-dimensional shaped chamber configured to operate at the operating pressure throughout the user's respiratory cycle and configured to receive a user's mouth and nares, wherein an inner surface of the body is spaced apart from the user, in use throughout the user's respiratory cycle; and a seal forming structure configured to form a seal against the user's face in use, the seal forming structure comprising:

a nose seal portion configured to extend around at least a portion of the user's nares on an inferior side of the user's nose inferior to the user's nasal ridge, and a mouth seal portion configured to form a seal at least partially around the user's mouth and between the chin and the lip inferior, the mouth seal connected to the nose seal to form a single, continuous seal, wherein an end of the nose seal portion is directly connected to an end of the mouth seal portion; and a positioning and stabilising structure to provide a force to hold the seal forming structure in position on the user's head wherein at least a portion of the body is configured to allow passage of air into and out of the three-dimensional shaped chamber.

In some forms: a) the three-dimensional shaped chamber includes a cupped chamber; b) the body includes a two-dimensional rigidized pattern to assist in maintaining the three-dimensional shaped chamber; c) the two-dimensional rigidized pattern radiates outwardly from a center of the body; d) the body includes a three-dimensional rigidizer to assist in maintaining the three-dimensional shaped chamber; and/or e) the three-dimensional rigidizer and the body are constructed from the same material.

In some forms: a) the body comprises a port through which air can enter and exit the three-dimensional shaped chamber; b) the body is substantially impermeable and air can only enter and exit the three-dimensional shaped chamber through the port, in use; and/or c) wherein at least a portion of the body is permeable, such that air can enter and exit the three-dimensional shaped chamber through a surface of the body.

In some forms: a) the nose seal portion includes a cantilever structure extending from the body toward the user's face in use; b) the cantilever structure is configured to form a seal around anterior and lateral portions of a periphery of the alar base of the user's nose; c) the cantilever structure of the nose seal portion is constructed using a one-piece construction; d) the cantilever structure is connected to the body using an adhesive, sewing, and/or ultrasonic welding; e) the cantilever structure includes an anterior edge that is at least partially linear; f) the positioning and stabilising structure is connected to the body in a parallel orientation with the anterior edge; g) a central portion configured to contact an inferior region of the user's nose proximate to the user's pronasale; h) a pair of lateral end portions configured to contact the user proximate the nasolabial sulcus; i) a pair of middle portions; j) each middle portion of the pair of middle portions between the central portion and one lateral end portion of the pair of lateral end portions; k) each middle portion configured to contact the user's face proximate to the alar base; l) the central portion of the cantilever structure seals to the user's face above the lip superior; m) the central portion of the cantilever structure does not form a seal above the user's lip superior directly inferior to the user's subnasale and nares; n) the middle portion of the cantilever structure forms a maximum width of the cantilever structure; and/or o) the middle portion extends approximately 20 mm from the body.

In some forms: a) the nose seal portion includes an anterior edge and a posterior edge configured to contact the user's face; b) each middle portion includes a maximum width between the anterior edge and the posterior edge; c) a lateral edge at each lateral end portion of the nose seal portion includes a minimum width between the anterior edge and the posterior edge; d) the lateral edge is connected to the mouth seal portion; e) the posterior edge is proximate to the middle portion is arcuate; f) the minimum width between the anterior edge and the posterior edge is substantially equal to a thickness of the mouth seal portion; g) a bridge is connected to the seal forming structure; h) the bridge extends between the maximum width of each middle portion; i) the bridge is constructed from an elastic material, and is connected to the seal forming structure under tension prior to use; j) the bridge is connected to a superior surface of the nose seal portion, the superior surface configured to contact the user, in use; k) the bridge does not contact the nose seal portion between the maximum width of each middle portion; l) the cantilever structure of the nose seal portion includes a first piece and a second piece joined at a central portion; and/or m) the first piece and the second piece being constructed from the same material and being symmetrical with respect to one another.

In some forms: a) the body is formed from a spacer fabric, a foam, and/or a thermoformed material; b) the body is formed form a rigid or semi-rigid material; c) the body maintains its three-dimensional shape so as to space an interior surface of the body away from the user's lips in use; d) the body is formed from a flat sheet and comprises at least one pleat; e) the cantilever structure is connected to the body using an adhesive, sewing, and/or ultrasonic welding; f) a central superior portion of a perimeter of the body is provided with a plastically deformable element that is configured to bend and change a shape of the body; and/or g) the plastically deformable element is constructed from metal.

In some forms: a) at least one filter element configured to filter air prior to entering and/or exiting the chamber; b) the at least one filter element is provided to an interior surface of chamber; c) the at least one filter element covers substantially the entire interior surface of the body; d) the interior surface includes at least one fastener, and wherein the filter element is configured to removably connected to the at least one fastener; e) the at least one fastener is formed from a hook and loop material; f) a rigid member is coupled to at least a portion of an outer perimeter of the filter element; g) the rigid member is resilient and configured to return to a neutral position after a compressive force is removed; h) the inner surface of the body includes a pocket, and wherein the filter element removably positionable within the pocket; i) an interior surface of the chamber includes at least one fastener; and/or j) the filter element is configured to removably connected to the at least one fastener.

In some forms: a) the position and stabilising structure comprises two elastic loops, each loop configured to engage one of the user's ears; b) the elastic loops are connected to the body around at least a majority of perimeter of body; c) the elastic loops are connected to the body around substantially an entire perimeter of the body; d) the two elastic loops each form a complete, unbroken perimeter; and/or e) the elastic loops are thicker proximate to the body, and taper toward a free end distal to the body.

In some forms: a) the nose seal portion is configured to not extend into the user's nares; b) the nose seal portion is constructed from a single piece of material; c) the nose seal portion is symmetric about a central portion configured to contact the user's nose proximate to the pronasale, in use; d) the cantilever structure includes an anterior edge that is at least partially linear; and/or e) the positioning and stabilising structure is connected to the body in a parallel orientation with the anterior edge.

In some forms: a) the body includes an outer surface and an edge between the outer surface and the inner surface; b) the positioning and stabilising structure connected to the edge; c) the positioning and stabilising structure is connected to the edge with an adhesive; d) the positioning and stabilising structure includes an upper arm and a lower arm each connected to the edge; e) the upper arm and the lower arm are oriented substantially tangential from a central portion of the nose seal portion; and/or f) the central portion configured to contact an inferior region of the user's nose proximate to the user's pronasale.

In some forms: a) the nose seal portion includes an anterior edge and a posterior edge configured to contact the user's face; b) the middle portion includes a maximum width between the anterior edge and the posterior edge; c) a lateral edge at each lateral end portion of the nose seal portion includes a minimum width between the anterior edge and the posterior edge; d) each lateral edge connected to the mouth seal portion; e) the posterior edge proximate to the middle portion is arcuate; and/or f) the minimum width between the anterior edge and the posterior edge is substantially equal to a thickness of the mouth seal portion.

In some forms: a) the cantilever structure of the nose seal portion is constructed using a one-piece construction; b) the cantilever structure of the nose seal portion includes a first piece and a second piece joined at a central portion; and/or c) the first piece and the second piece being constructed from the same material and being symmetrical with respect to one another.

In some forms: a) ports or passages evenly distributed over the surface of the body and may allow airflow into and/or out of the chamber; b) the ports or passages may be positioned to direct airflow away from the user's eyes to avoid irritation or fogging if glasses are worn; c) passages or ports may be located toward the bottom of the body to direct air in the anterior, inferior, and/or lateral direction; d) a valve or flap may be included over at least some of the ports or passages; e) the valve or flap may be a one-way valve and may allow airflow inhaled into the chamber, but may block airflow exhaled out of the chamber; and/or f) the port or passage may include auxetic material (or other adaptive materials) in order to adjust (e.g., reduce) the diameter of the ports or passages during use in order to change the volumetric flow rate through the particular ports or passages.

Another form of the present technology comprises a mask for use at an operating pressure substantially equal to atmospheric pressure, the mask comprising:

a body defining a chamber configured to operate at the operating pressure and configured to receive a user's mouth and nares; and a deformable member coupled to a superior portion of the body, wherein the deformable member is configured to be positioned proximate to the user's nose inferior to the user's pronasale, in use;

a seal forming structure configured to form a seal against the user's face in use, the seal forming structure comprising:
  a nose seal portion configured to extend around at least a portion of the user's nares on an inferior side of the user's nose, and
  a mouth seal portion configured to form a seal at least partially around the user's mouth,
  wherein an end of the nose seal portion is directly connected to an end of the mouth seal portion; and
a positioning and stabilising structure to provide a force to hold the seal forming structure in position on the user's head;

wherein at least a portion of the body is configured to allow passage of air into and out of the chamber; and wherein the body and/or nose seal portion are selectively movable to conform to the user's face and the deformable member is plastically deformable and configured to maintain a selected shape.

Another example of the present technology comprises a mask for use at an operating pressure equal to atmospheric pressure, the mask comprising:

a body forming a chamber configured to operate at the operating pressure through the user's respiratory cycle and configured to receive a user's mouth and nares; and a seal forming structure configured to form a seal against the user's face in use, the seal forming structure comprising:
  a nose seal portion configured to extend around at least a portion of the user's nares on an inferior side of the user's nose, the nose seal portion including a cantilever structure extending from the body toward the user's face in use, the cantilever structure configured to form a seal around anterior and lateral portions of a periphery of the alar base of the user's nose, the cantilever structure including an anterior edge connected to the body, a posterior edge opposite the anterior edge and configured to contact the user, a central portion including a first width between the anterior edge and the posterior edge, the central portion configured to contact an inferior region of the user's nose proximate to the user's pronasale, a pair of lateral end portions configured to contact the user proximate the nasolabial sulcus, each lateral end portion of the pair of lateral end portions including a second width between the anterior edge and the posterior edge, the second width being less than the first width, and a pair of middle portions, each middle portion of the pair of middle portions between the central portion and one lateral end portion of the pair of lateral end portions, each middle portion includes a third width between the anterior edge and the posterior edge, the third width being greater than the first width, each middle portion configured to contact the user's face proximate to the alar base, and a mouth seal portion configured to form a seal at least partially around the user's mouth and between the chin and the lip inferior, the mouth seal connected to the pair of lateral ends to form a single, continuous seal, wherein an end of the nose seal portion is directly connected to an end of the mouth seal portion; and a positioning and stabilising structure to provide a force to hold the seal forming structure in position on the user's head;

wherein at least a portion of the body is configured to allow passage of air into and out of the chamber.

Another form of the present technology comprises a mask for use at an operating pressure substantially equal to atmospheric pressure, the mask comprising:

a body defining a chamber configured to operate at the operating pressure and configured to receive a user's mouth and nares, the body including at least one fastening member;

a filter removably positionable within the chamber and removably connected to the at least one fastening member;

a seal forming structure configured to form a seal against the user's face in use, the seal forming structure comprising:

a nose seal portion configured to extend around at least a portion of the user's nares on an inferior side of the user's nose, and a mouth seal portion configured to form a seal at least partially around the user's mouth, wherein an end of the nose seal portion is directly connected to an end of the mouth seal portion; and a positioning and stabilising structure to provide a force to hold the seal forming structure in position on the user's head;

wherein at least a portion of the body is configured to allow passage of air into and out of the chamber; and wherein the filter is configured to substantially cover an inner surface of the body so that inhaled and exhaled air passes through the filter.

Another form of the present technology comprises a method for constructing a hygiene mask, the method comprising:

providing a substantially flat sheet of material;

forming a pleat in the sheet of material and folding the sheet of material to form a substantially cup-shaped body, wherein the surface of the folded sheet of material being substantially free from wrinkles;

connecting a nasal seal portion to the cup-shaped body, the nasal seal portion extending in a cantilever portion from the body, the nasal seal portion being more impermeable than the sheet of material;

connecting a mouth seal to the cup-shaped body and to the nasal seal portion, the combination of the nasal seal portion and the mouth seal portion forming a complete seal perimeter;

connecting a positioning and stabilizing structure to a surface of the body substantially perpendicular to a surface connected to the nasal seal portion, the positioning and stabilizing structure extending around substantially the entire perimeter of the body.

Another form of the present technology comprises a method of using a hygiene mask, the method comprising:

providing the hygiene mask comprising a chamber, a seal forming structure, and a positioning and stabilising structure;

positioning the hygiene mask in an operating position against a user's face, wherein the user's nares and mouth are received within the chamber;

securing the positioning and stabilising structure to the user's head;

sealing the hygiene mask against the user's face using a force provided by the securing; and subsequently, maintaining substantially atmospheric pressure within the chamber throughout the user's entire respiratory cycle.

Another form of the present technology comprises a method of using a hygiene mask, the method comprising:

providing the hygiene mask with a chamber;

donning the hygiene mask inferior to the user's nasal ridge;

sealing the hygiene mask against the user's face and directing inhaled and exhaled air through a body of the mask; and subsequently to sealing, maintaining substantially atmospheric pressure within the chamber throughout the user's entire respiratory cycle.

Another form of the present technology comprises a method of using a hygiene mask, the method comprising:

donning the hygiene mask including a body forming a three-dimensional shaped chamber;

sealing a seal forming structure against the user's face to direct inhaled and exhaled air through the body; and subsequently to sealing, maintaining substantially atmospheric pressure within the three-dimensional shaped chamber throughout the user's entire respiratory cycle.

In some forms: a) the method further comprising positioning the seal forming structure against the user's face to contact a perimeter formed by an inferior region of the user's nose proximate to the user's pronasale, a middle region proximate to proximate to the alar base, a lateral region proximate to the nasolabial sulcus, and the region between the user's chin and lip inferior; b) the body is formed from a permeable or semi-permeable material; c) the method further comprises receiving the user's nares and mouth so that substantially all inhaled and exhaled air passes through the body; and/or d) the method further comprising adjusting the width of the body by bending a deformable member, the deformable member maintaining its position after a force is removed.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including:

RESPIRATORY SYSTEM AND FACIAL ANATOMY

Figure 1:
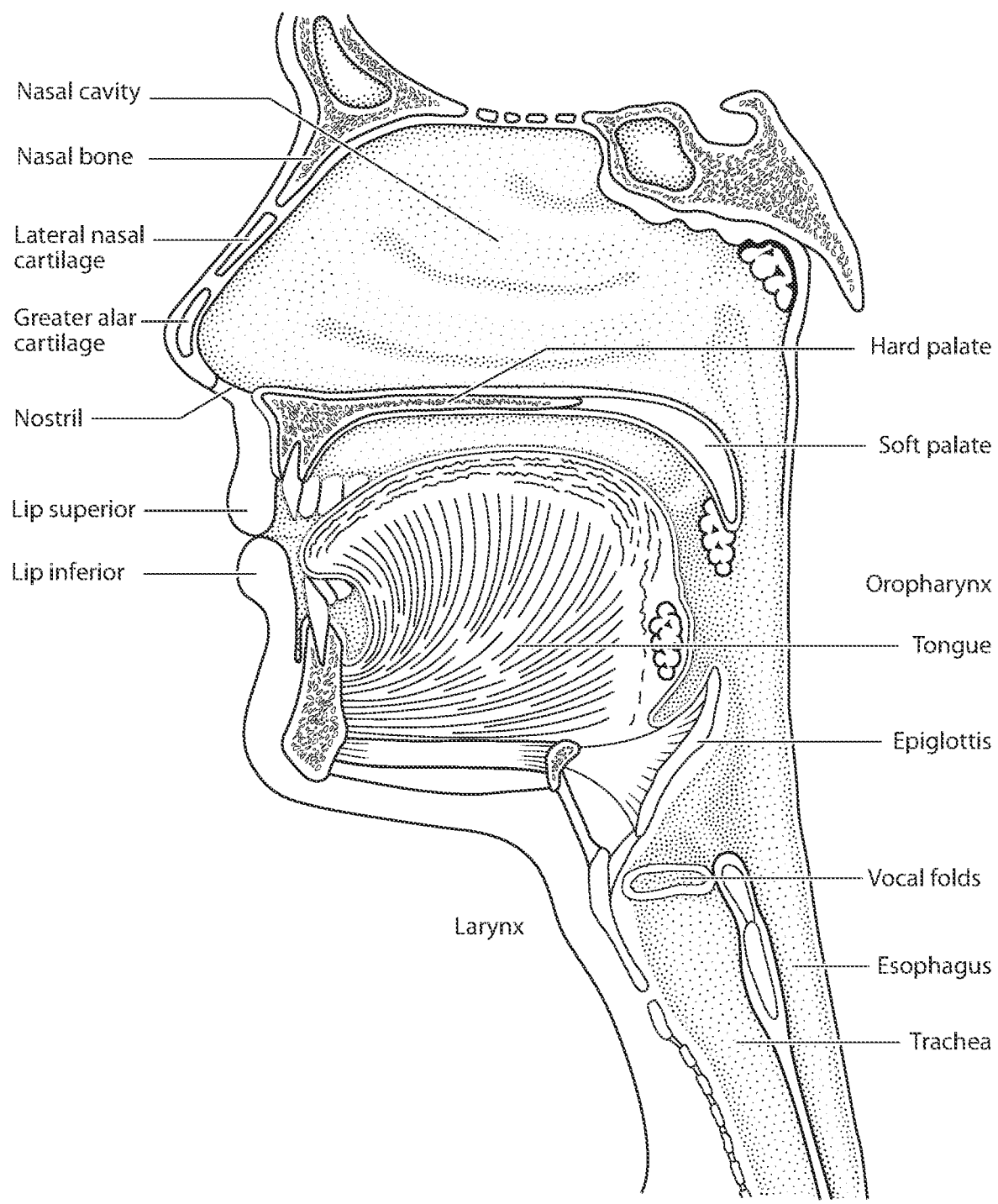

FIG. 1 shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2:
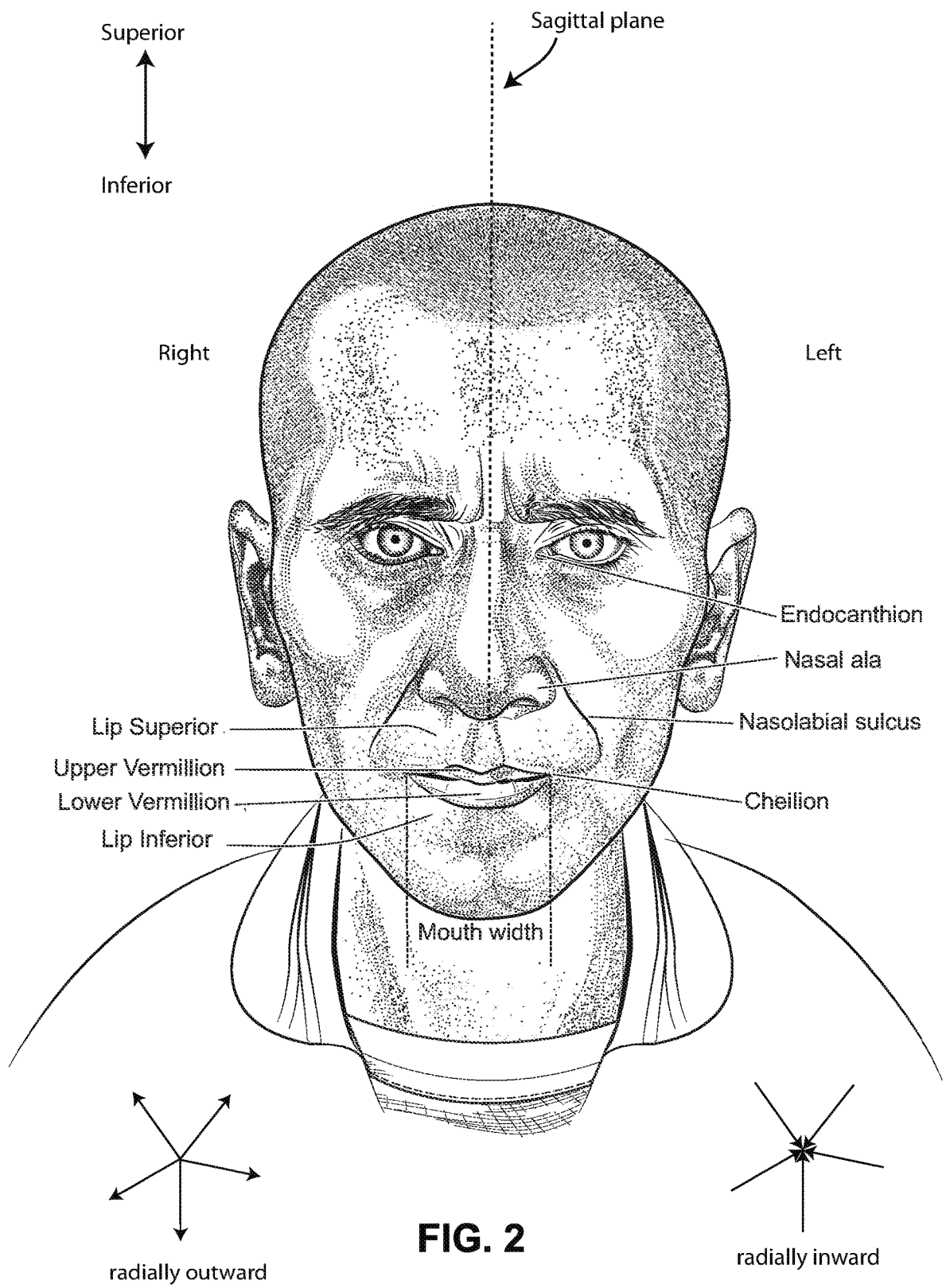
Figures 1, 2:
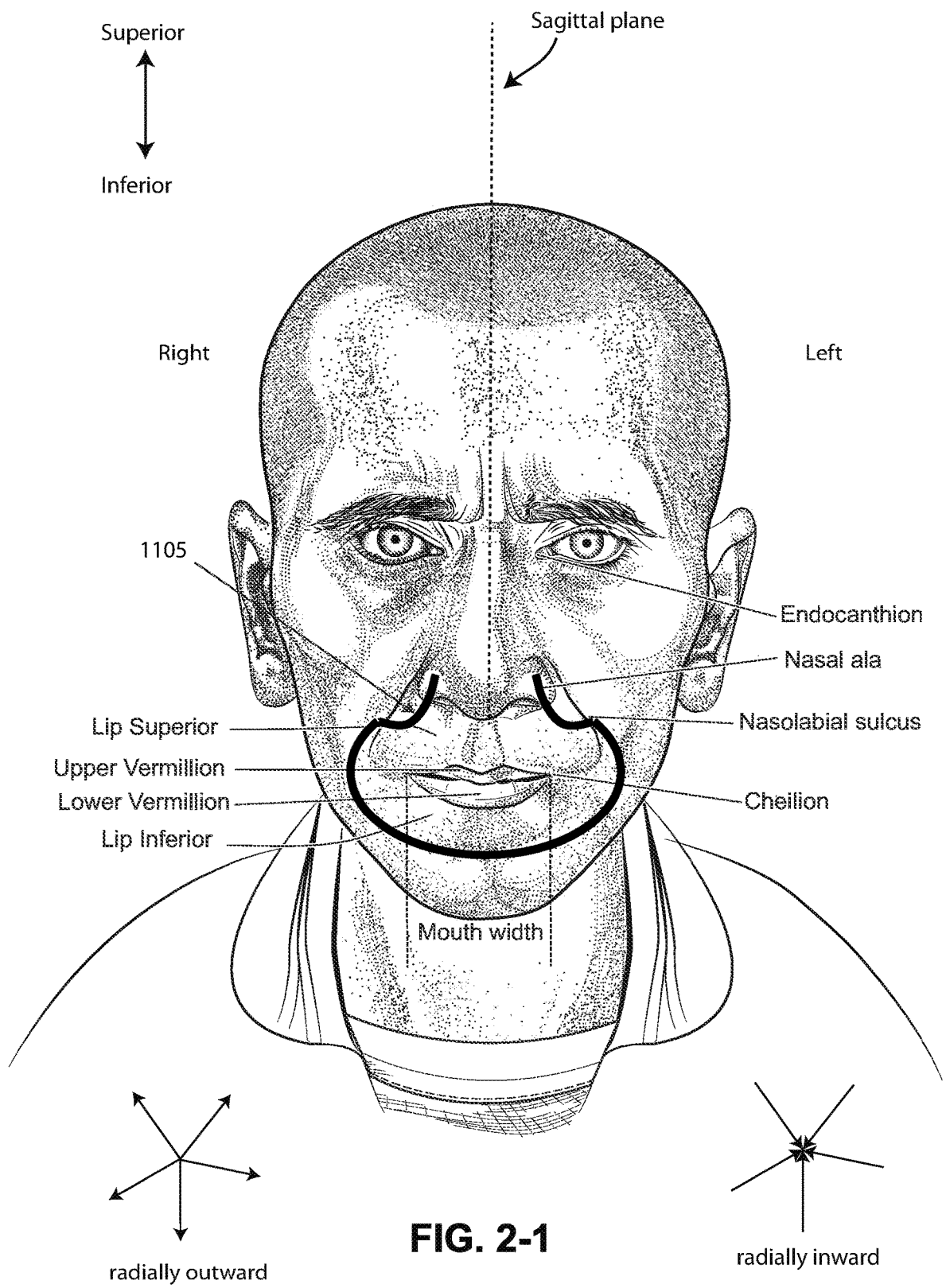

FIG. 2 is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

FIG. 2-1 is a front view of a face illustrating an outer perimeter of a seal contacting region along the user's face.

Figure 3:
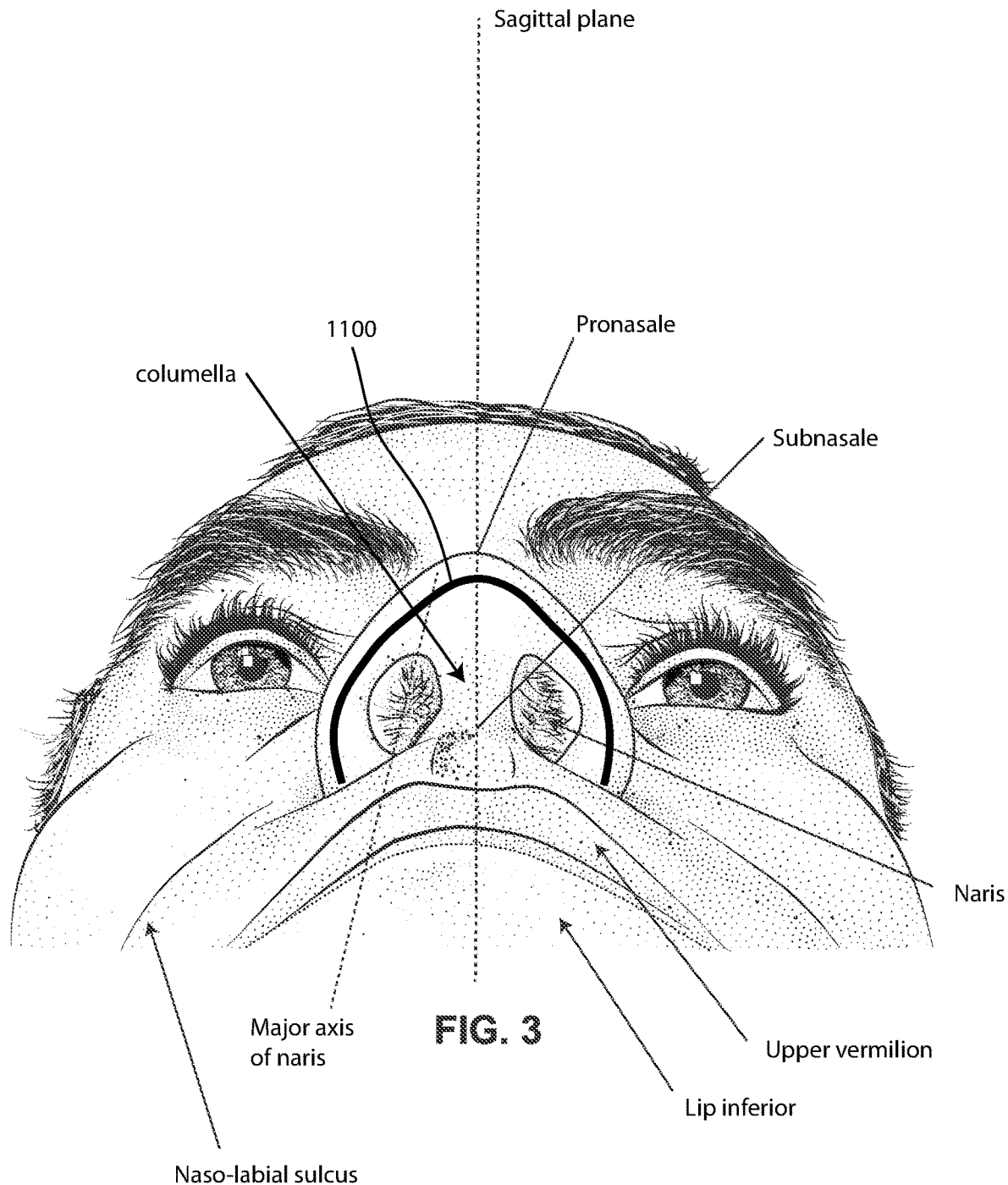
Figures 1, 3:
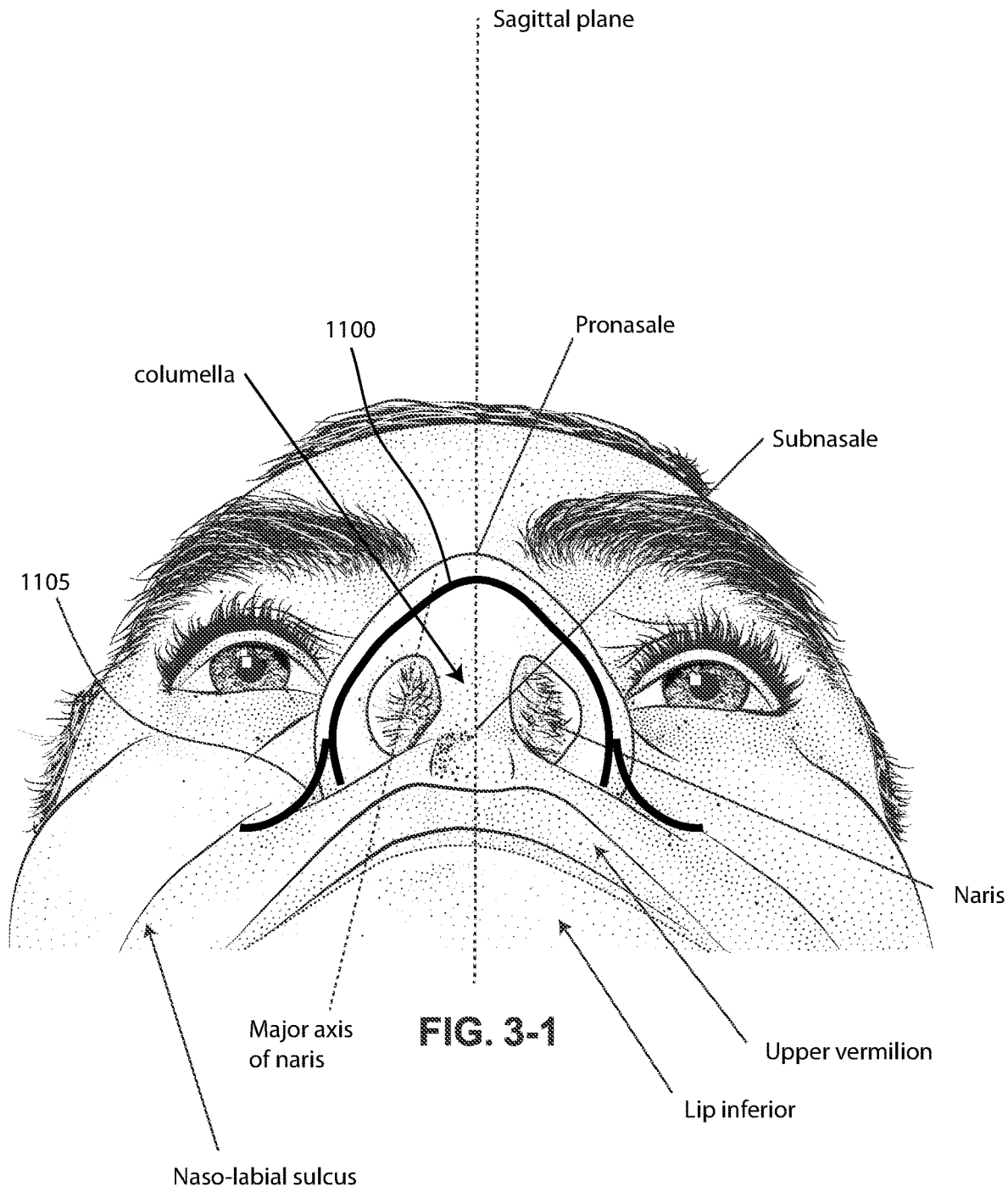

FIG. 3 shows a base view of a nose with several features identified including naso-labial sulcus, lip inferior, upper Vermilion, naris, subnasale, columella, pronasale, the major axis of a naris and the midsagittal plane.

FIG. 3-1 shows a base view of a nose illustrating a contact region of a seal against the nose.

DRAWINGS OF EXAMPLES OF THE PRESENT TECHNOLOGY

Figure 4:
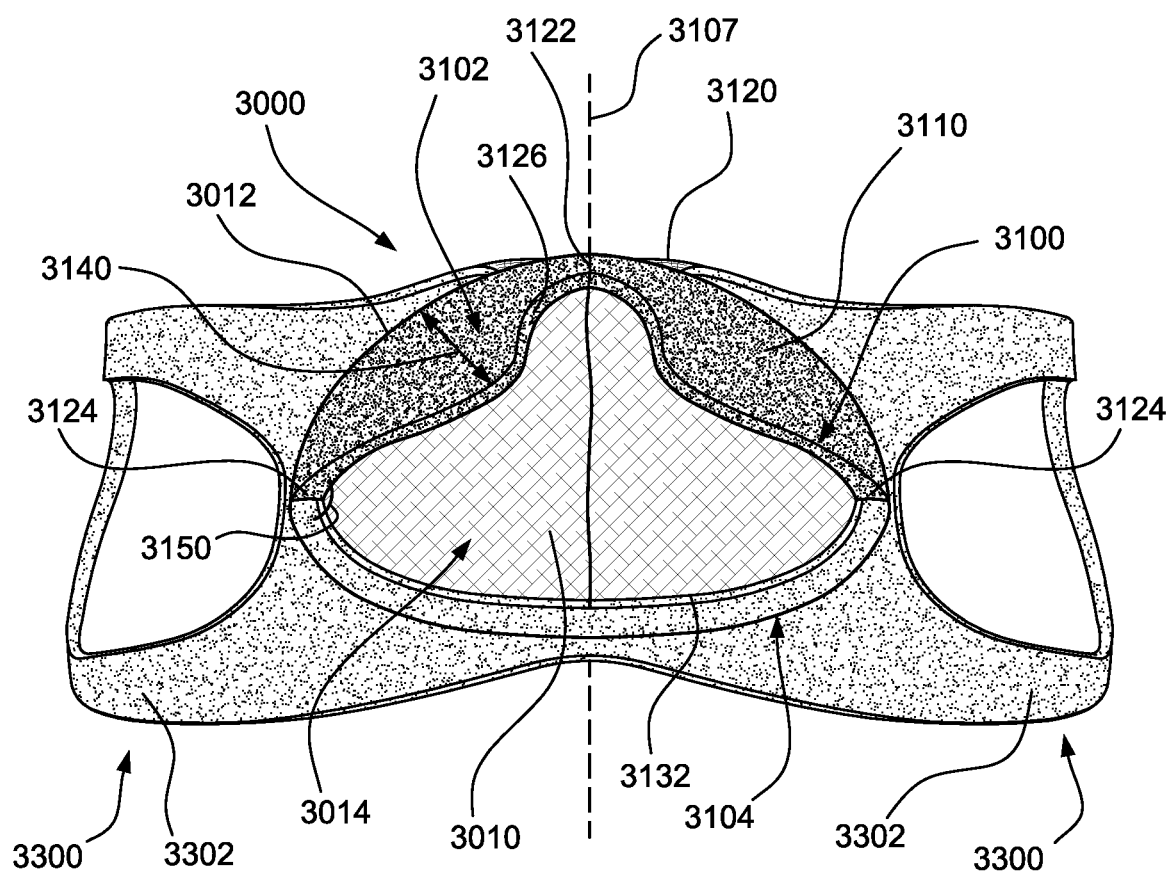
Figures 1, 4:
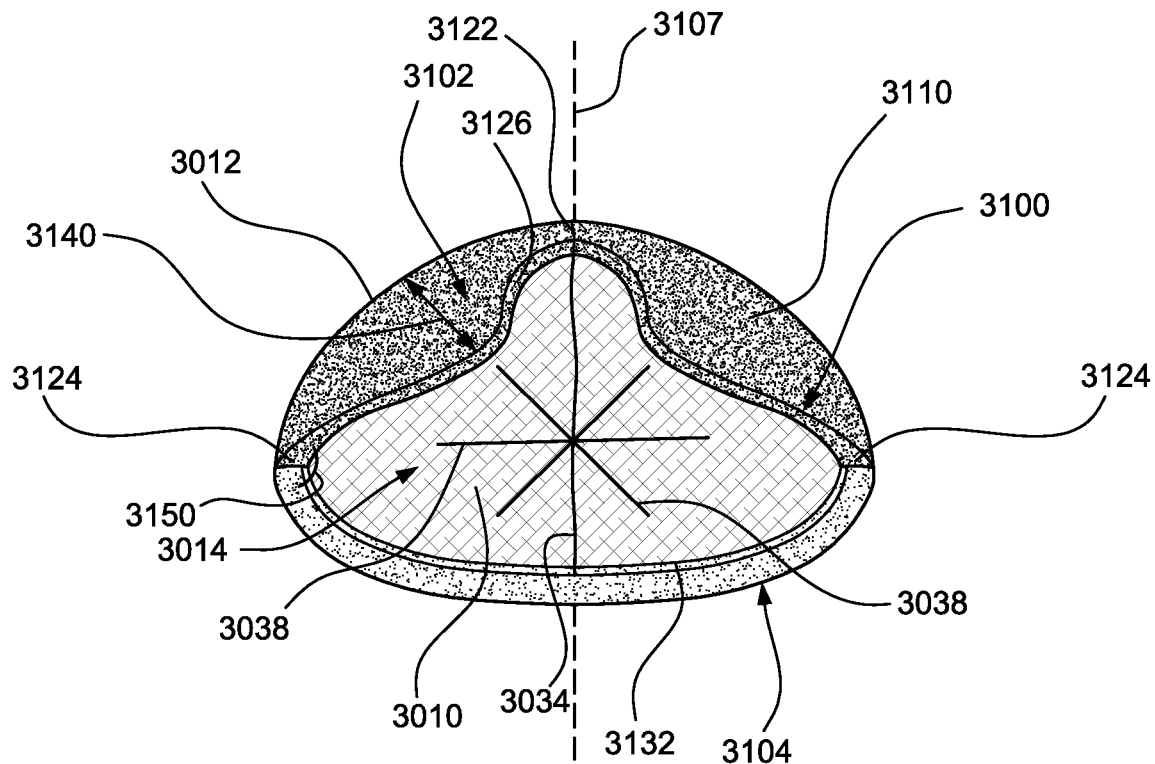
Figures 2, 4:
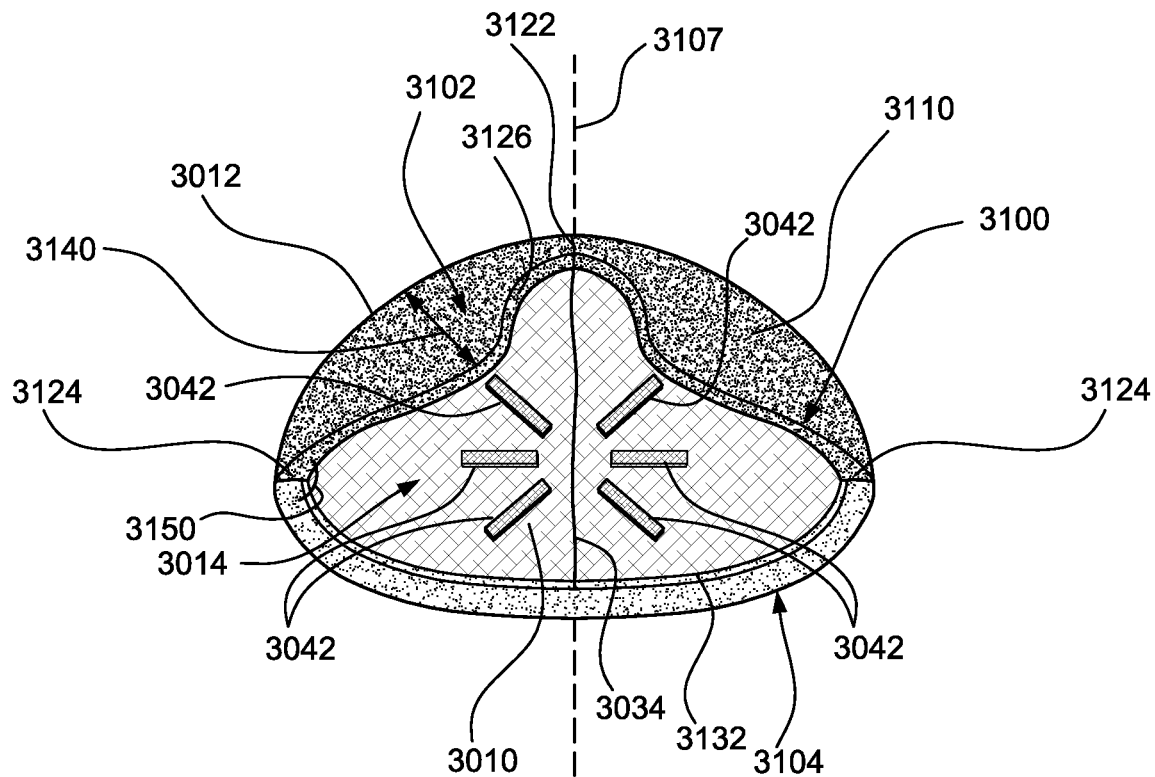

FIG. 4 is a rear view of a hygiene mask according to one form of the present technology.

FIG. 4-1 is a rear view of an alternate hygiene mask according to another form of the present technology including a two-dimensional rigidized pattern.

FIG. 4-2 is a rear view of an alternate hygiene mask according to another form of the present technology including three-dimensional rigidizers.

Figure 5:
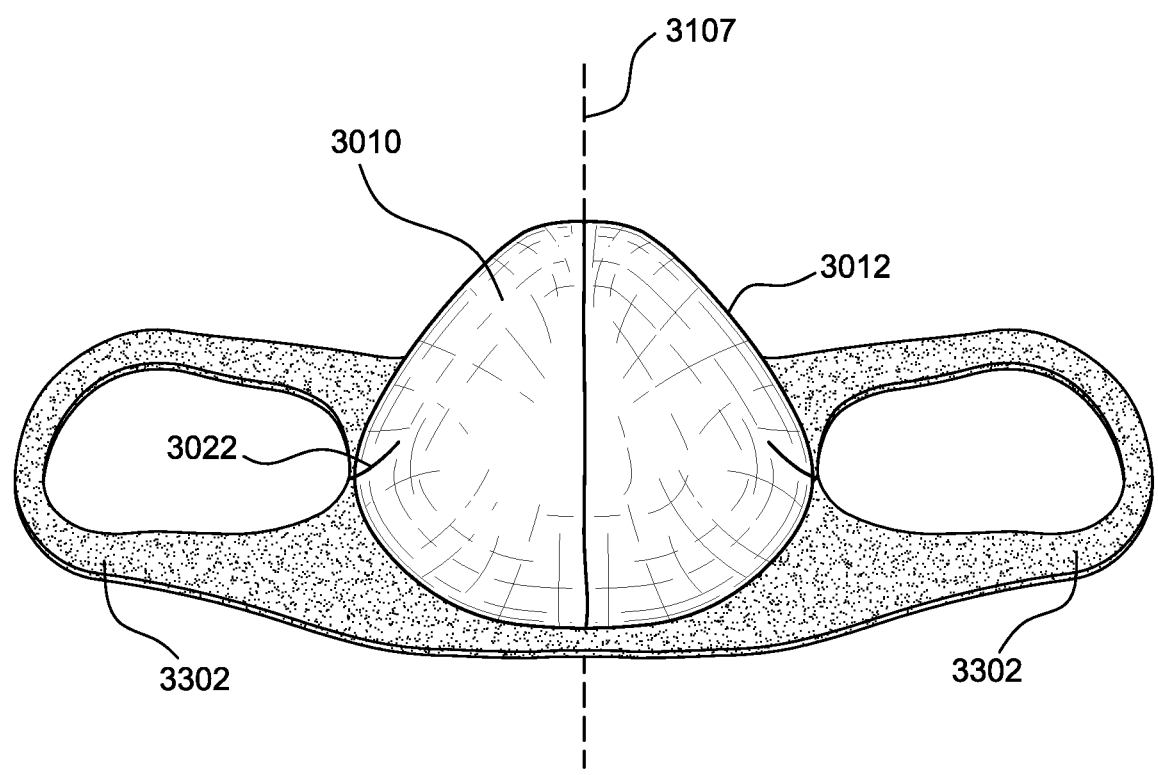
Figures 1, 5:
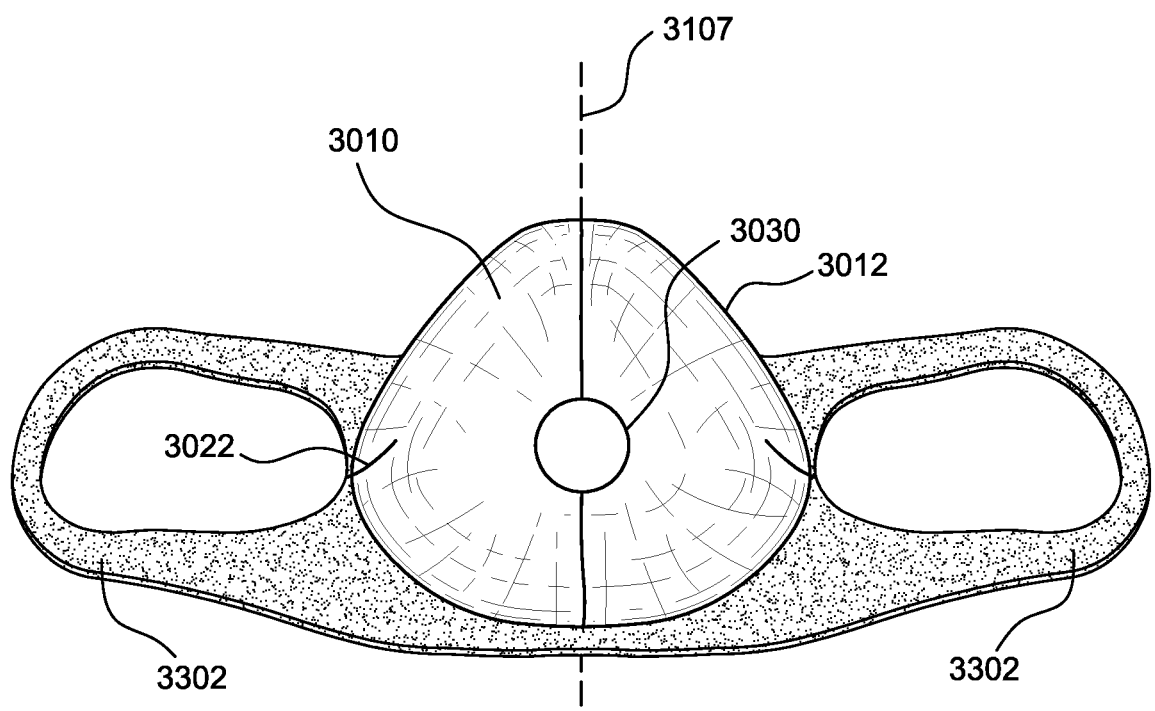
Figures 2, 5:
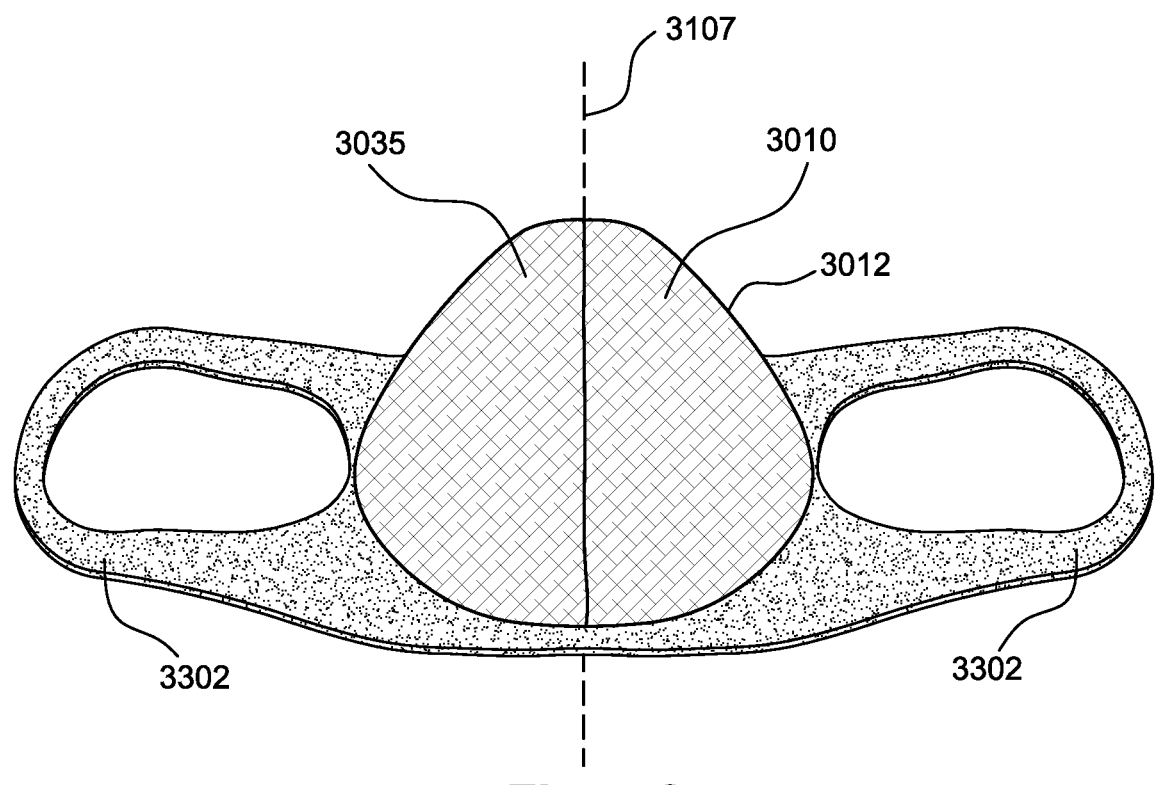

FIG. 5 is a front view of the mask of FIG. 4.

FIG. 5-1 is a front view of another example of a mask, which includes a port for allowing airflow into and out of the chamber.

FIG. 5-2 is a front view of another example of a mask, including a v-fold material to improve aesthetics of the mask.

Figure 6:
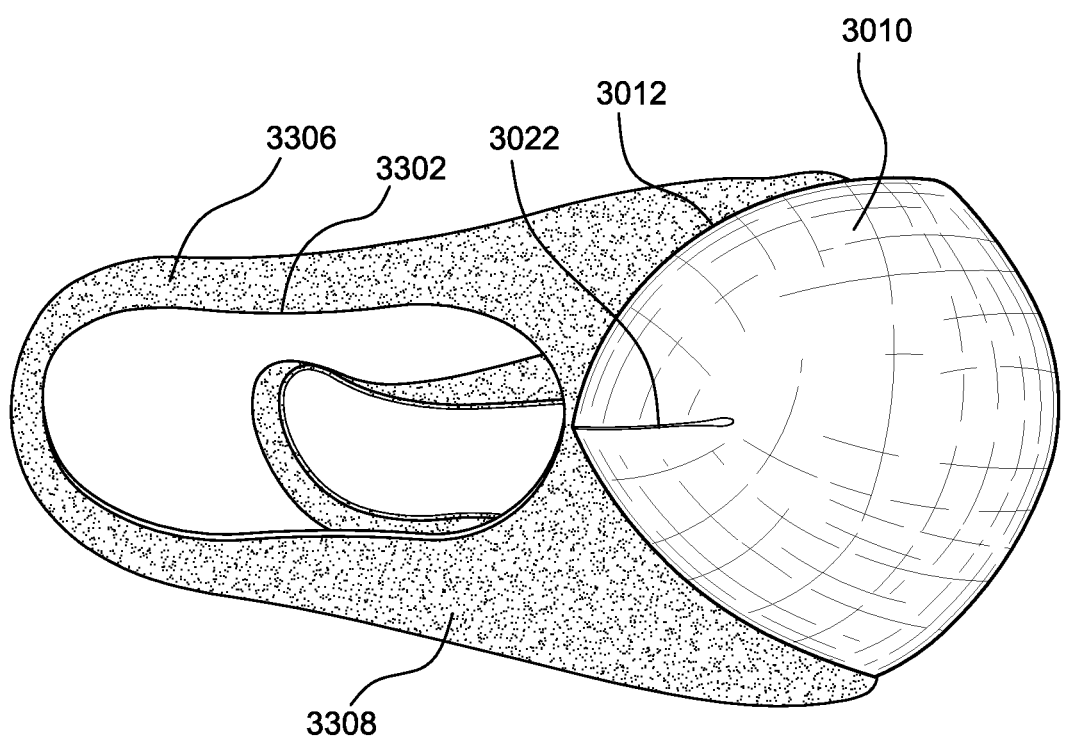

FIG. 6 is a side view of the mask of FIG. 4 with the headgear loops held back.

Figure 7:
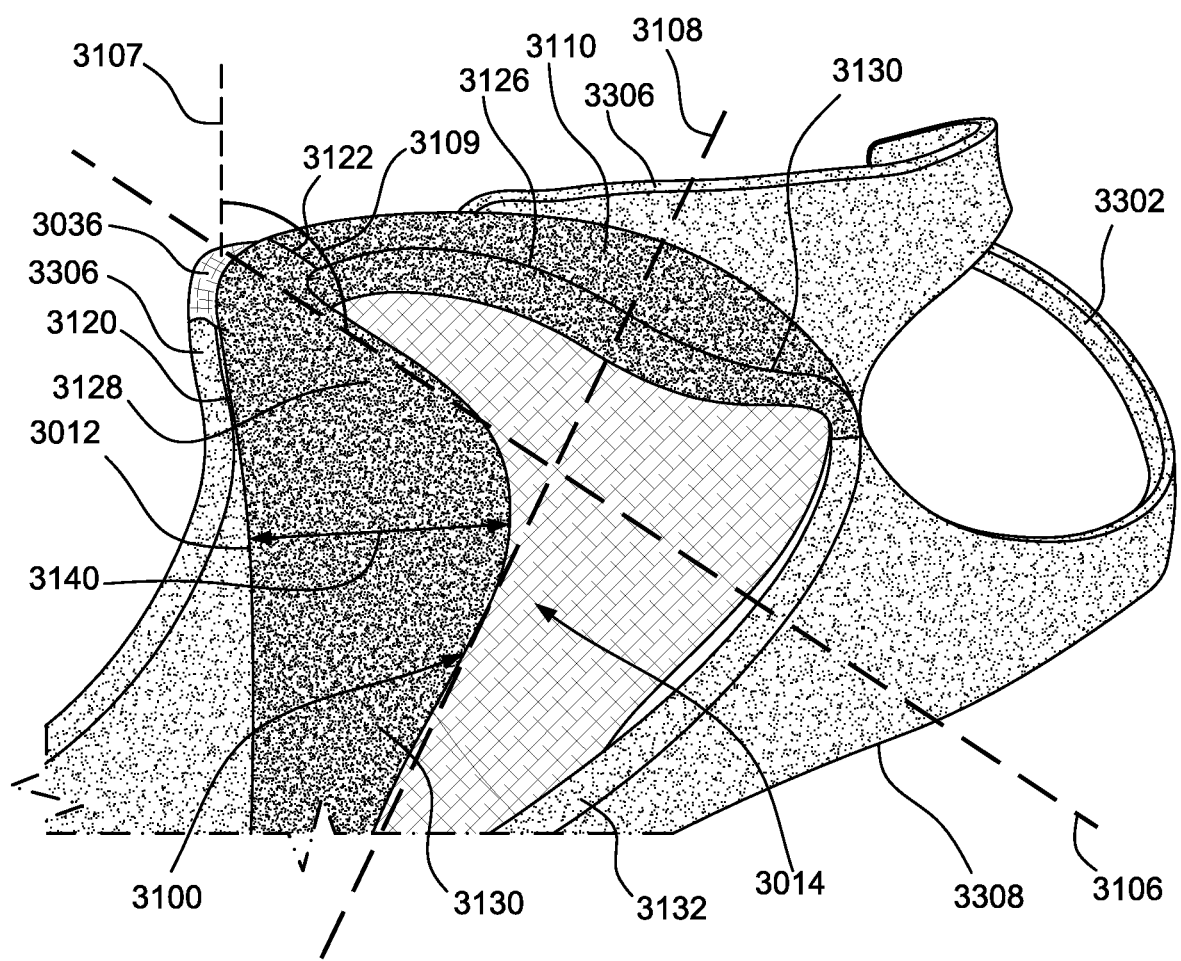

FIG. 7 is a perspective view from behind and above of the mask of FIG. 4.

Figure 8:
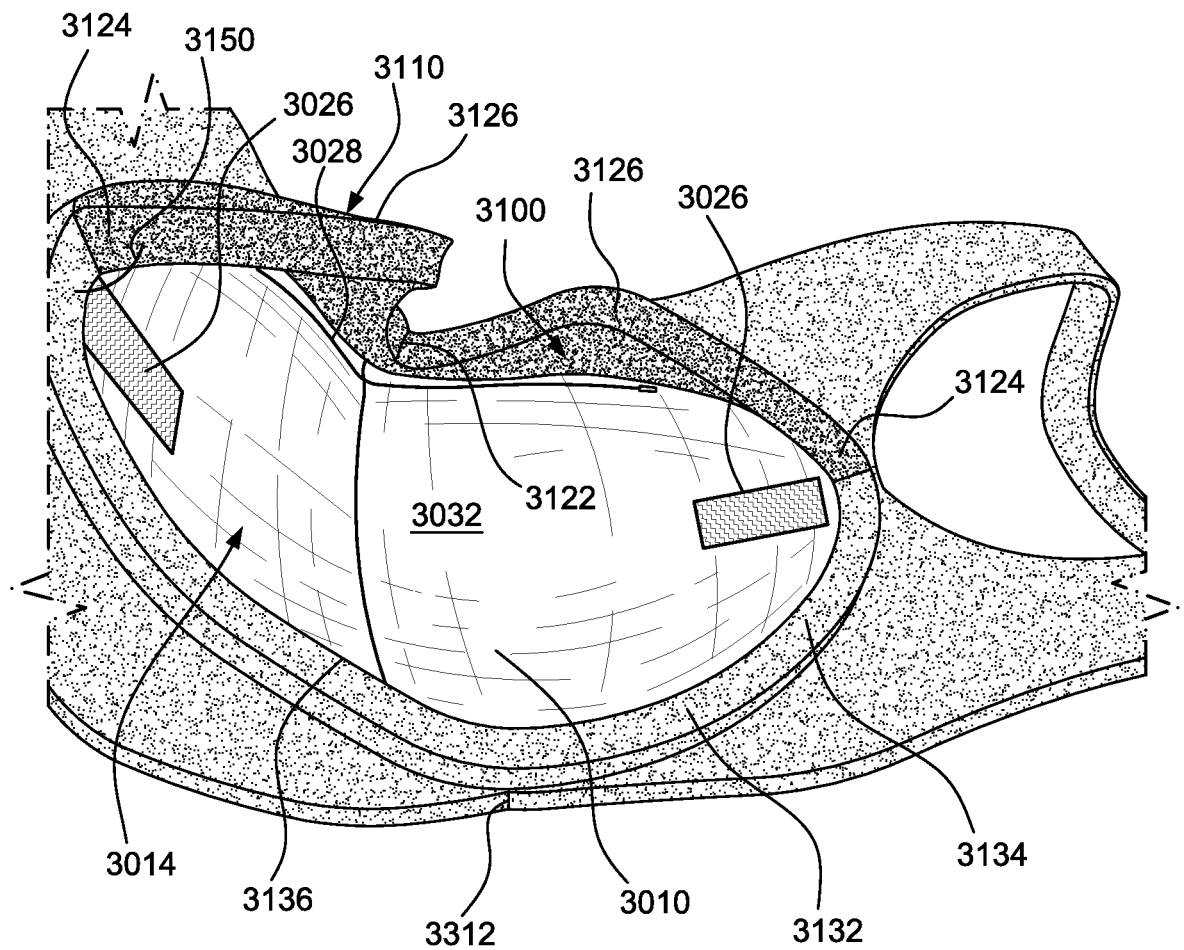
Figures 1, 8:
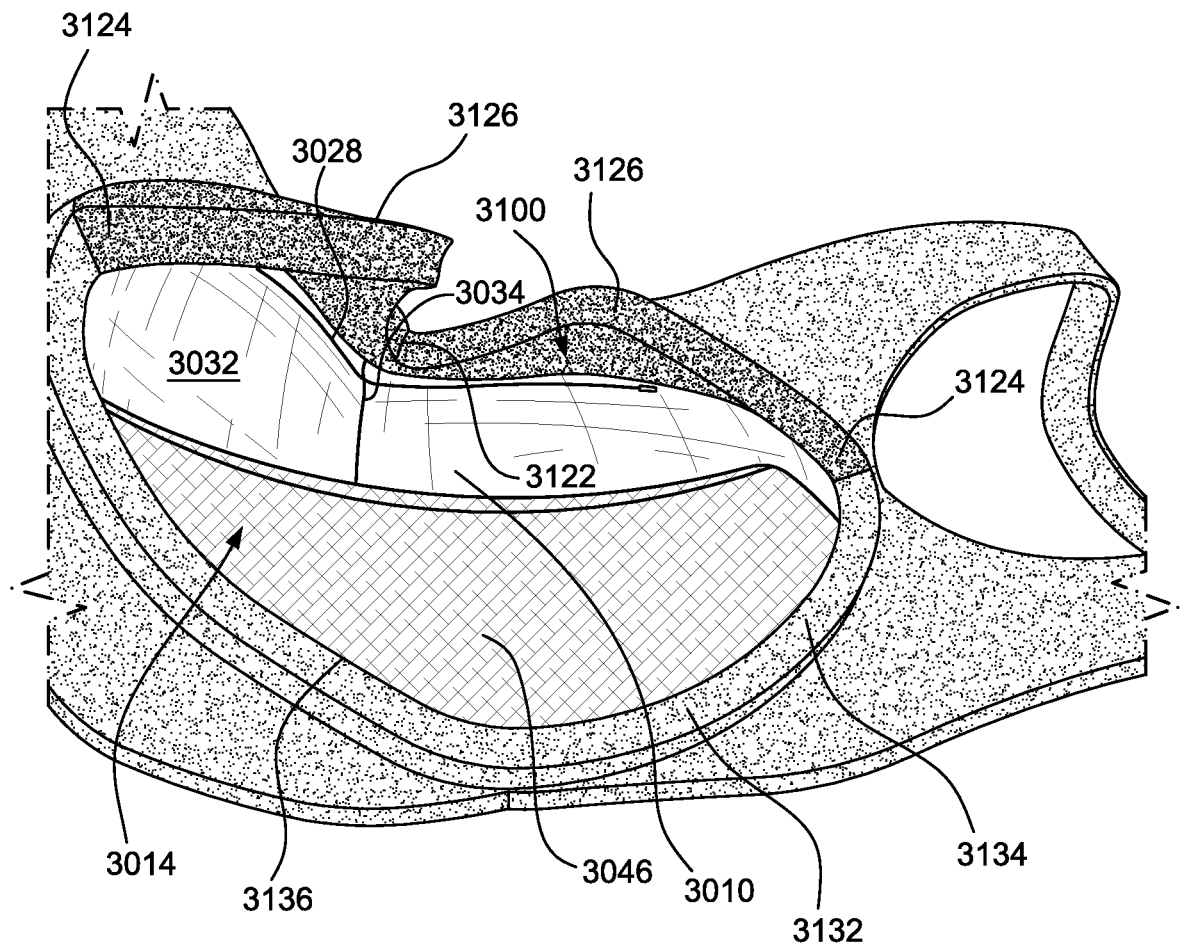

FIG. 8 is a perspective view from behind and below of the mask of FIG. 4.

FIG. 8-1 is a perspective view from behind and below of an alternate example of a mask, illustrating a pocket on an inner surface of the mask body.

Figure 9:
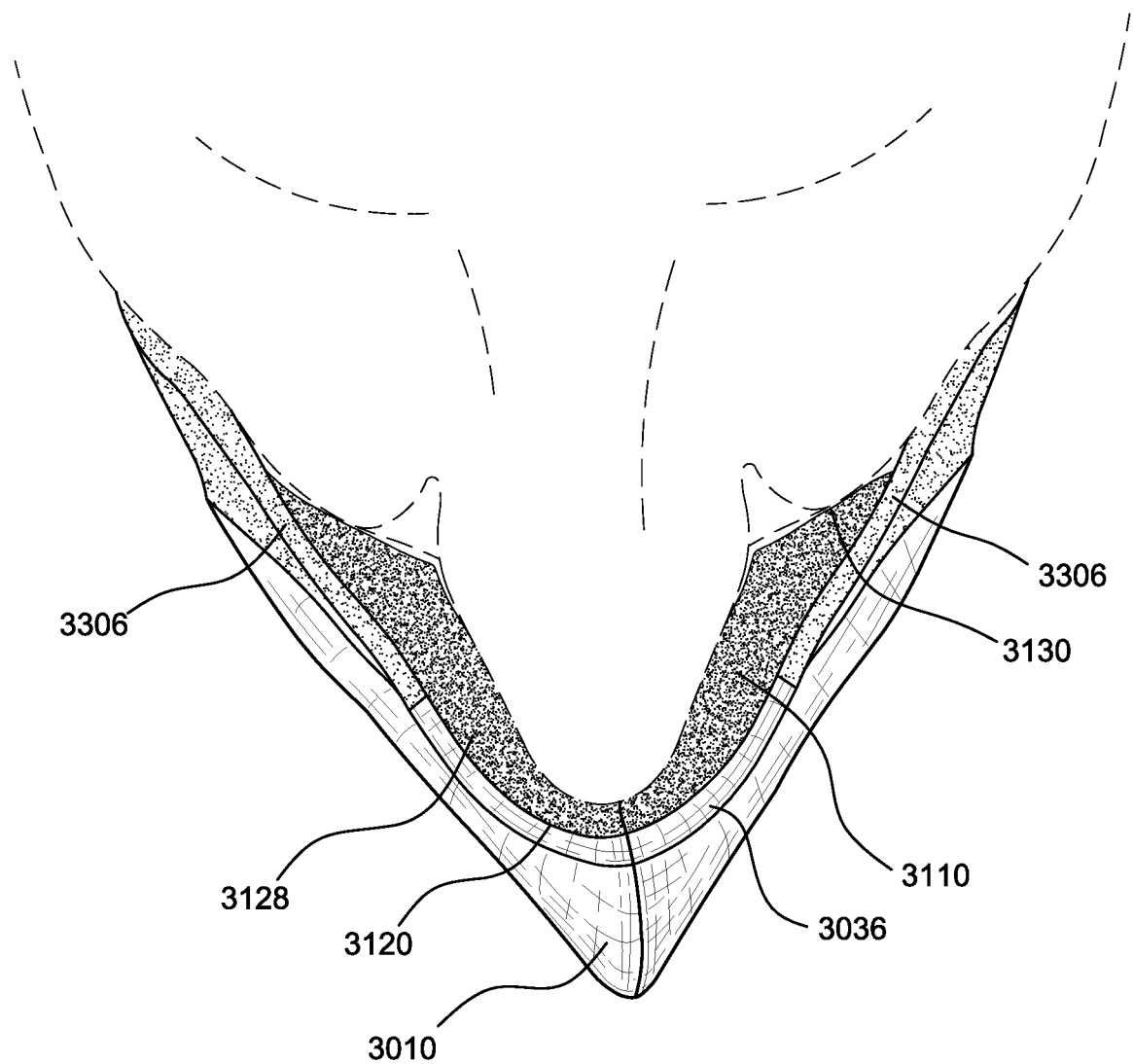
Figures 1, 9:
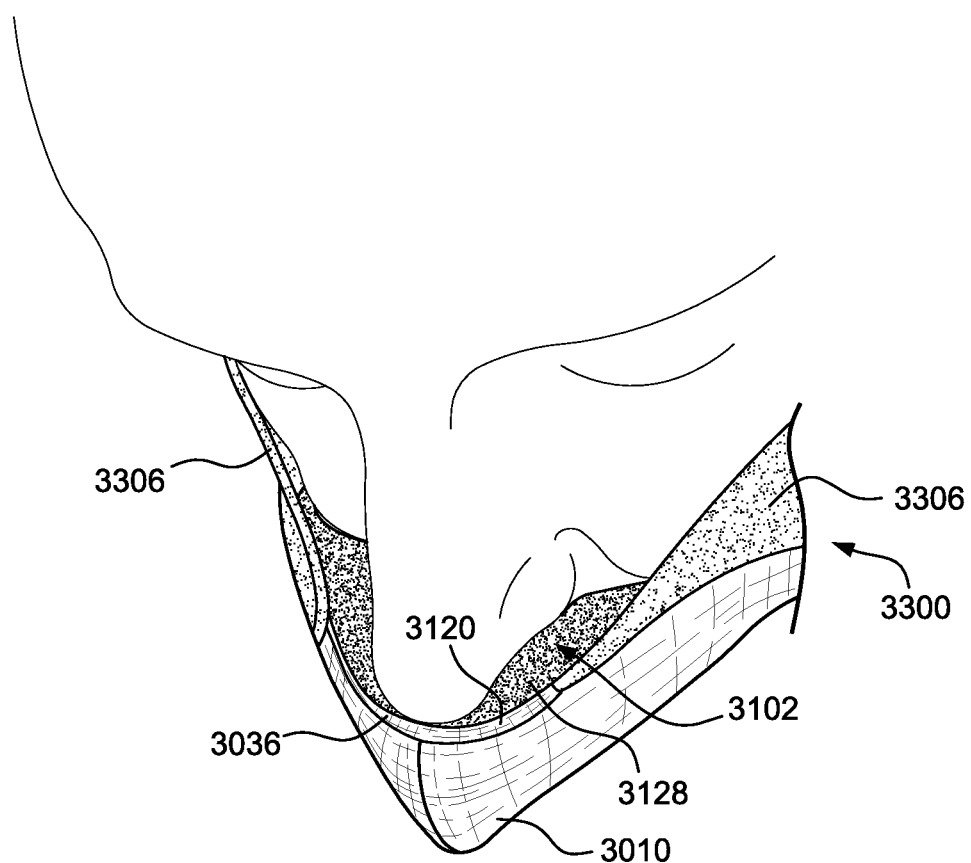

FIG. 9 is a top view of the mask of FIG. 4 in an in-use position on a user.

FIG. 9-1 is a top perspective view of the mask of FIG. 4 in an in-use position on a user.

Figure 10:
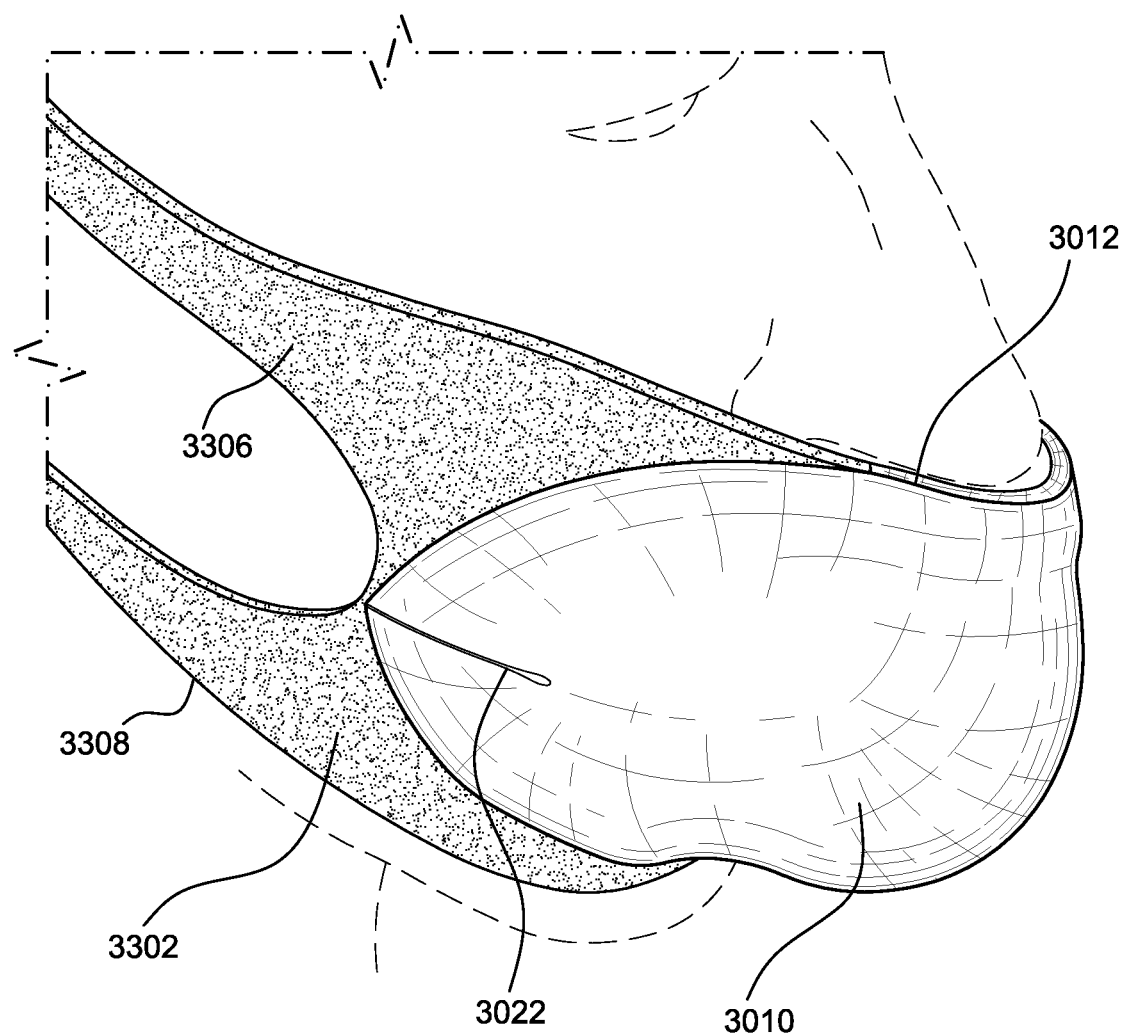

FIG. 10 is a front perspective view of the mask of FIG. 4 in an in-use position on a user.

Figure 11A:
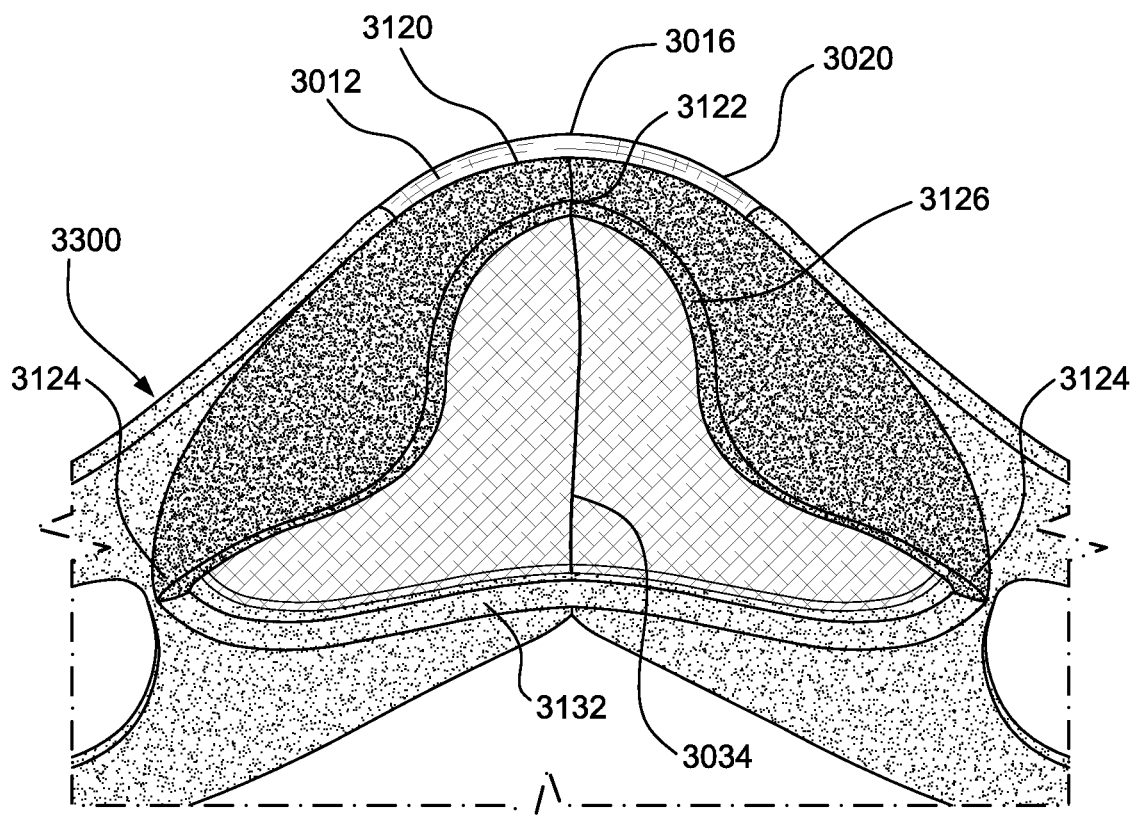

FIG. 11A is top view of the mask of FIG. 4 set for use by a user with a relatively wide nose.

Figure 11B:
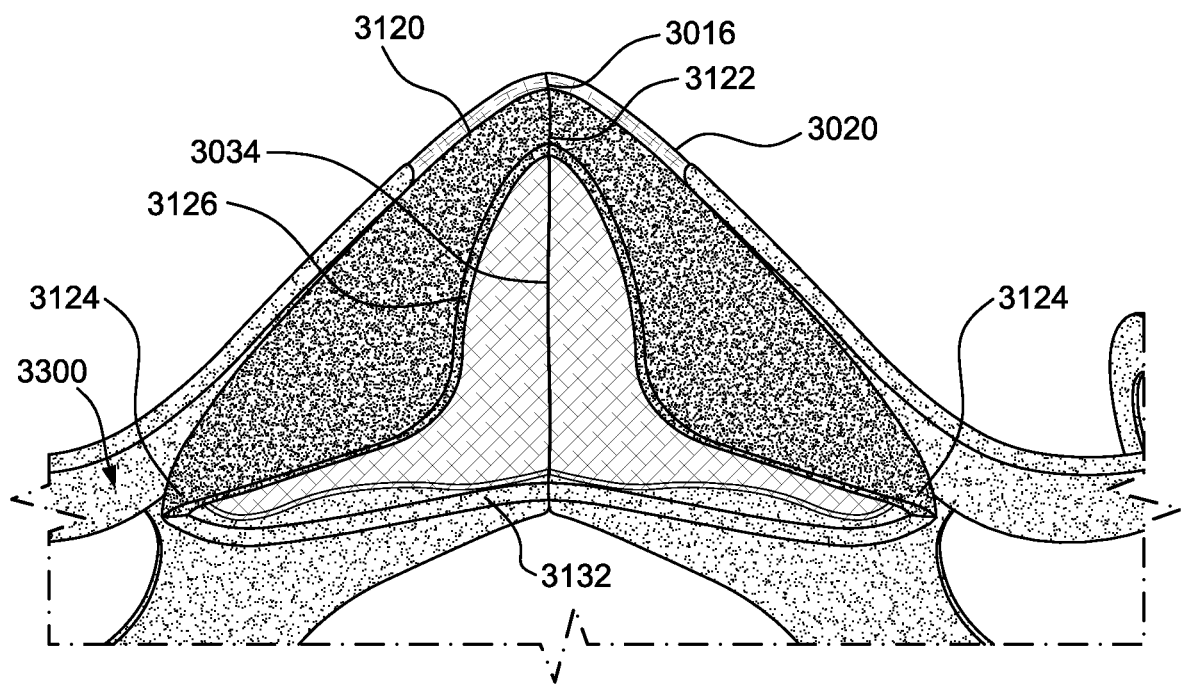

FIG. 11B is top view of the mask of FIG. 4 set for use by a user with a narrower nose.

Figure 12:
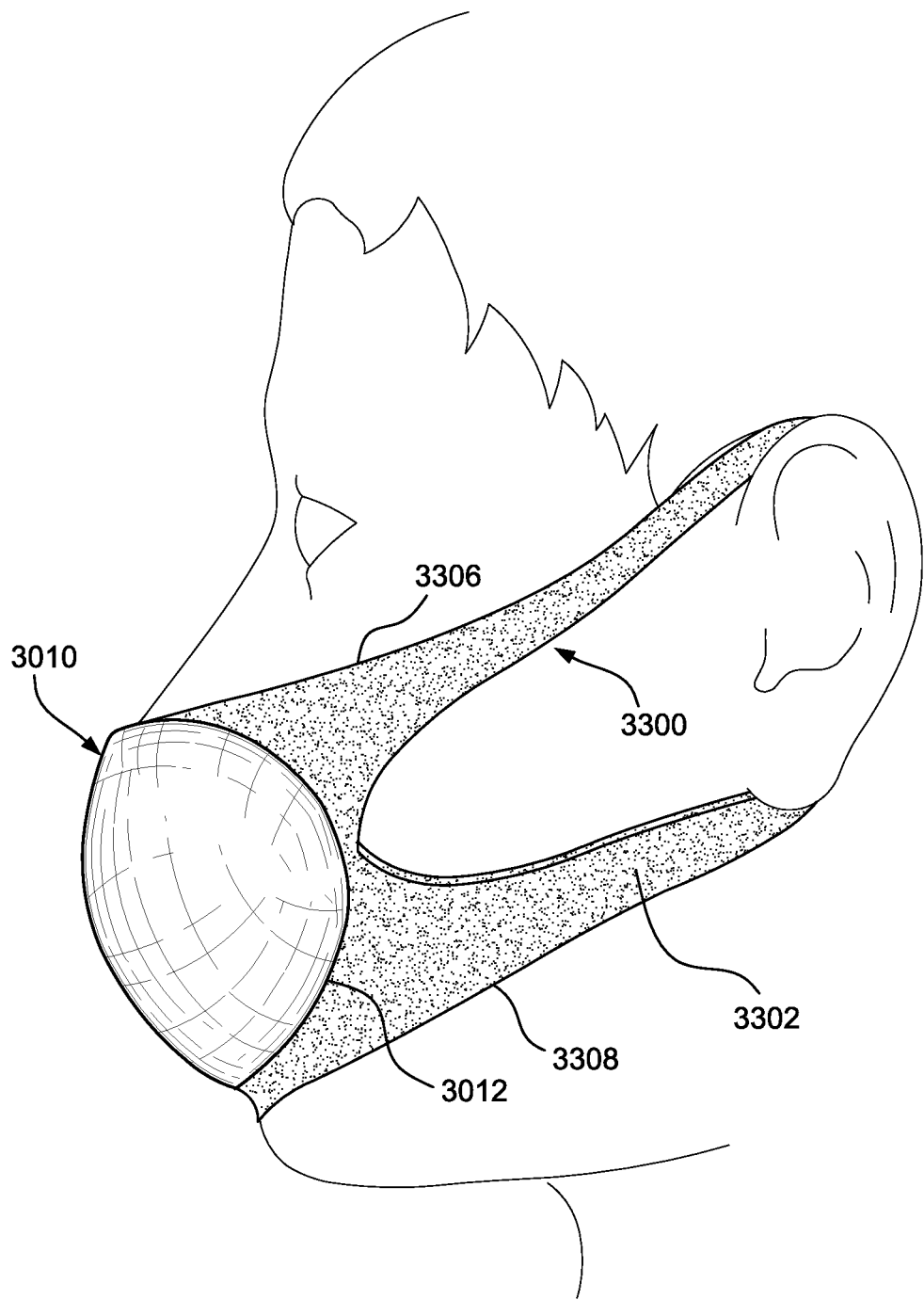

FIG. 12 is a side view of the mask of FIG. 4 in an in-use position on a user.

Figure 13:
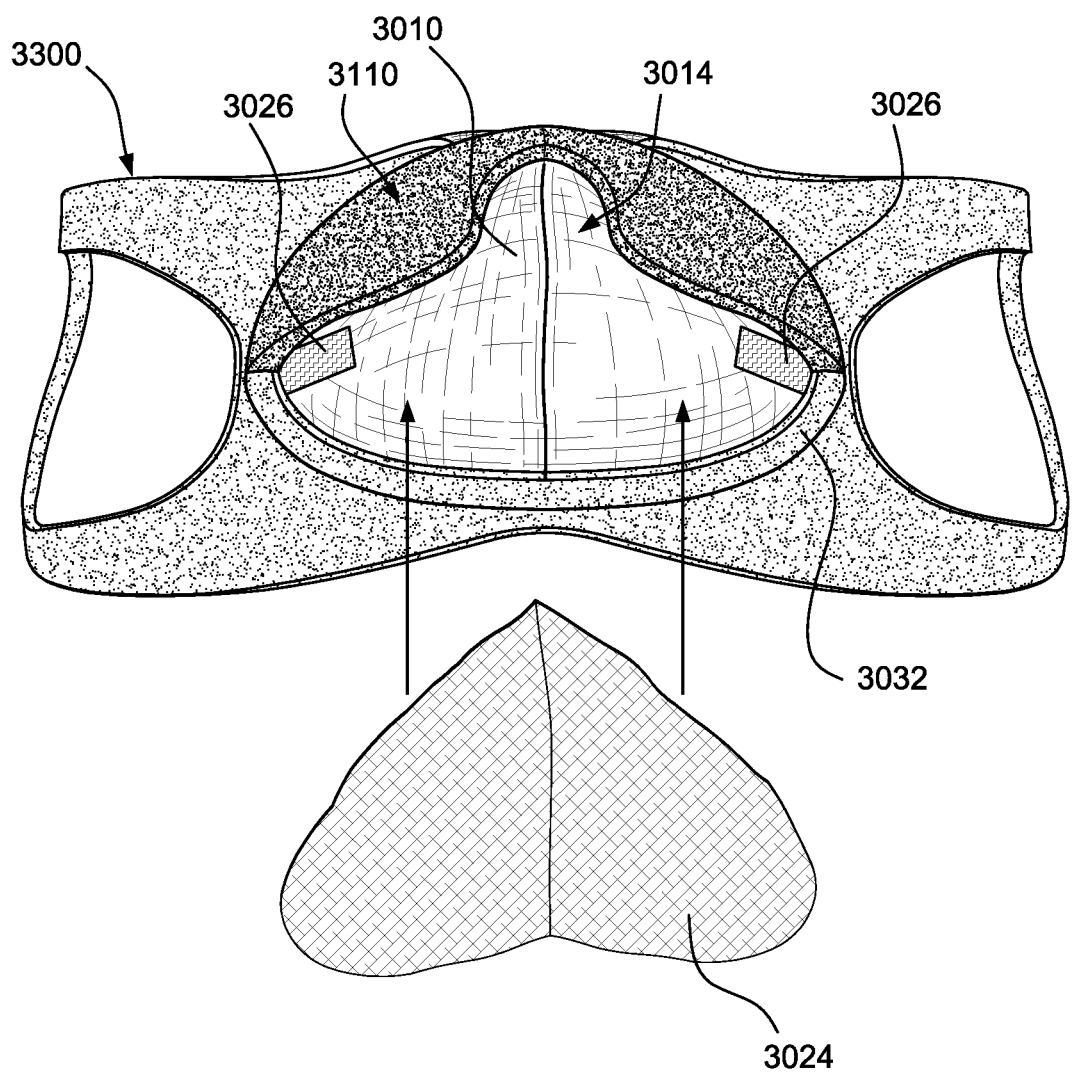
Figures 1, 13:
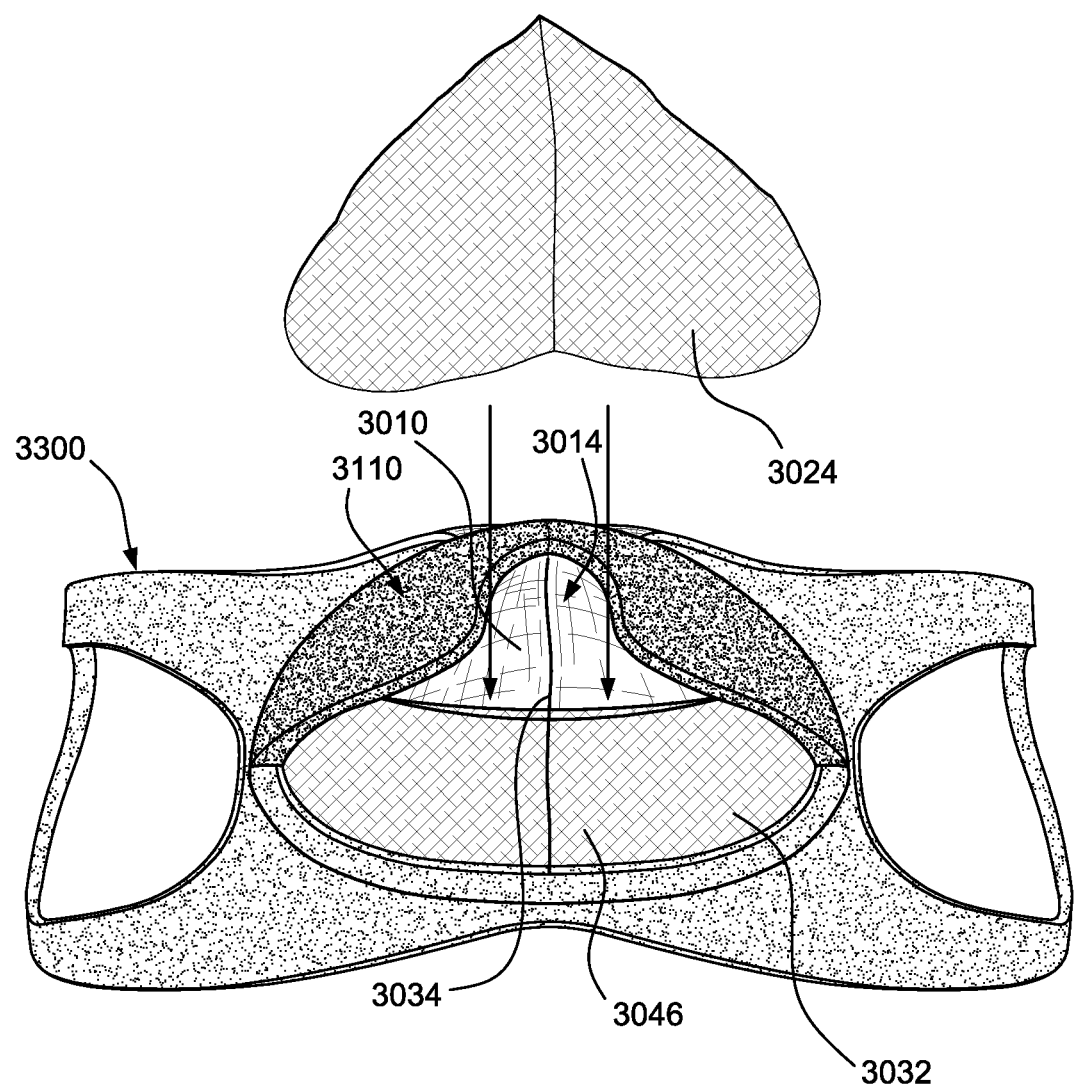
Figures 2, 13:
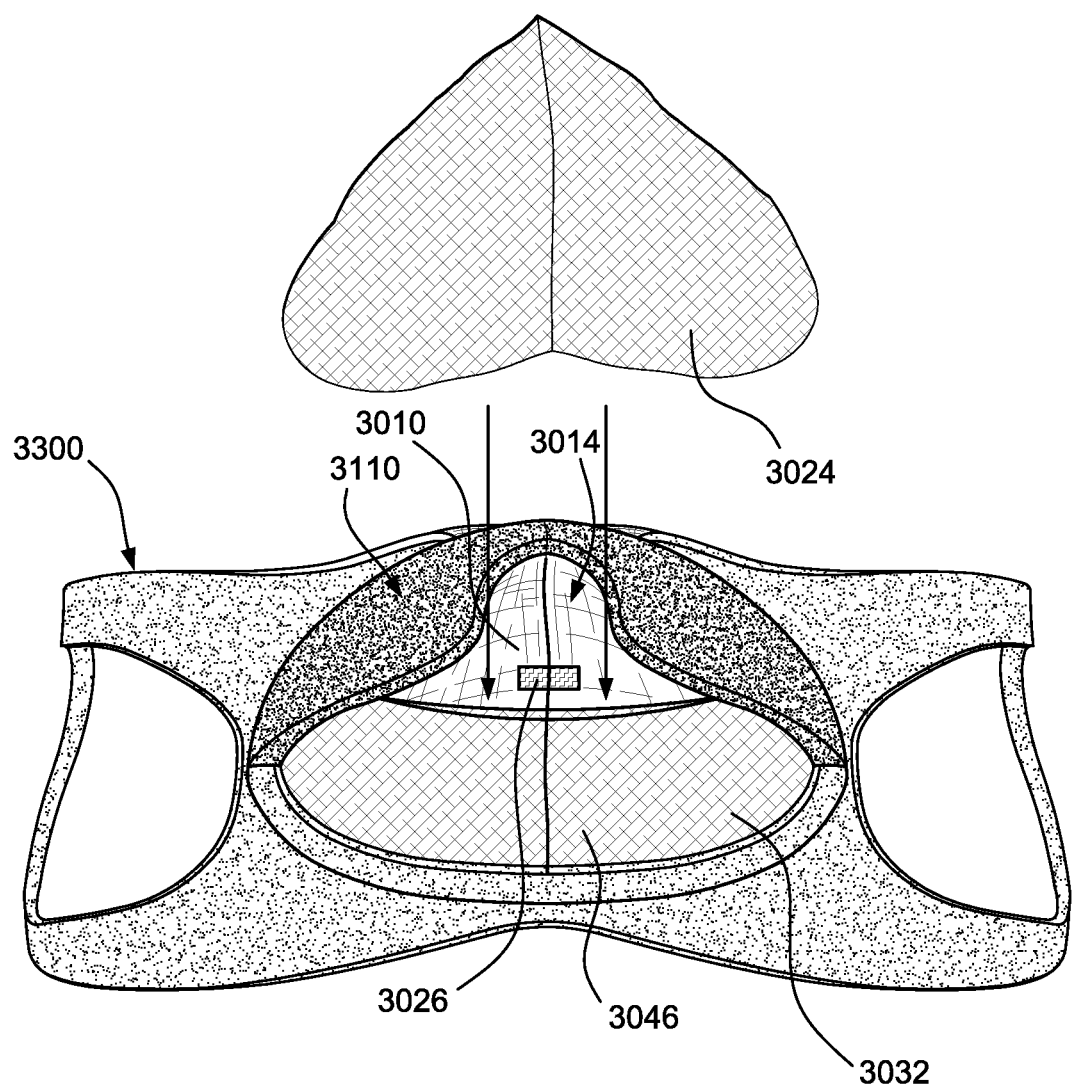

FIG. 13 is a rear perspective view of the mask of FIG. 4 with a filter element separated from the body.

FIG. 13-1 is a rear perspective view of another example of a mask with a filter element separated from the body.

FIG. 13-2 is a rear perspective view of another example of a mask with a filter element separated from the body.

Figures 1, 14:
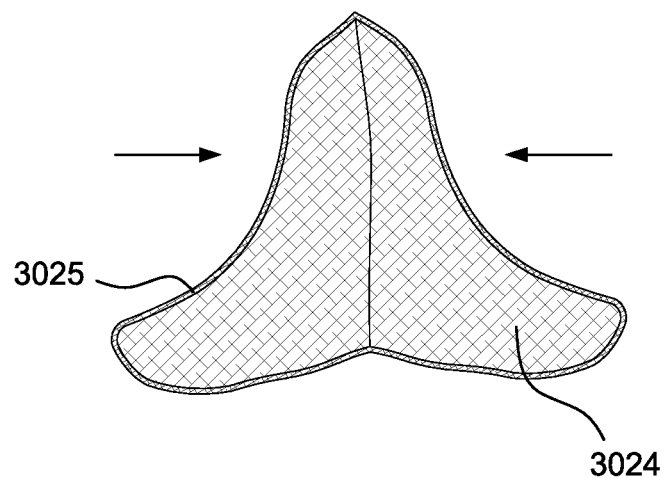
Figures 2, 14:
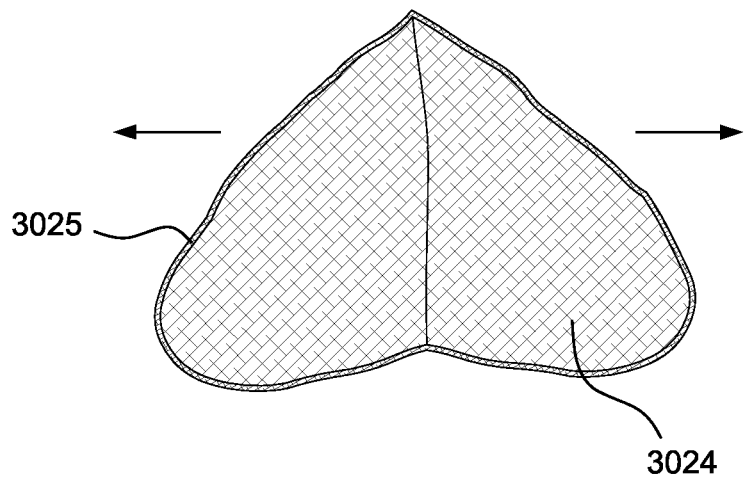

FIG. 14-1 is a front view of the filter element of FIG. 13 in a compressed position.

FIG. 14-2 is a front view of the filter element of FIG. 13 returning to a relaxed position.

Figure 15:
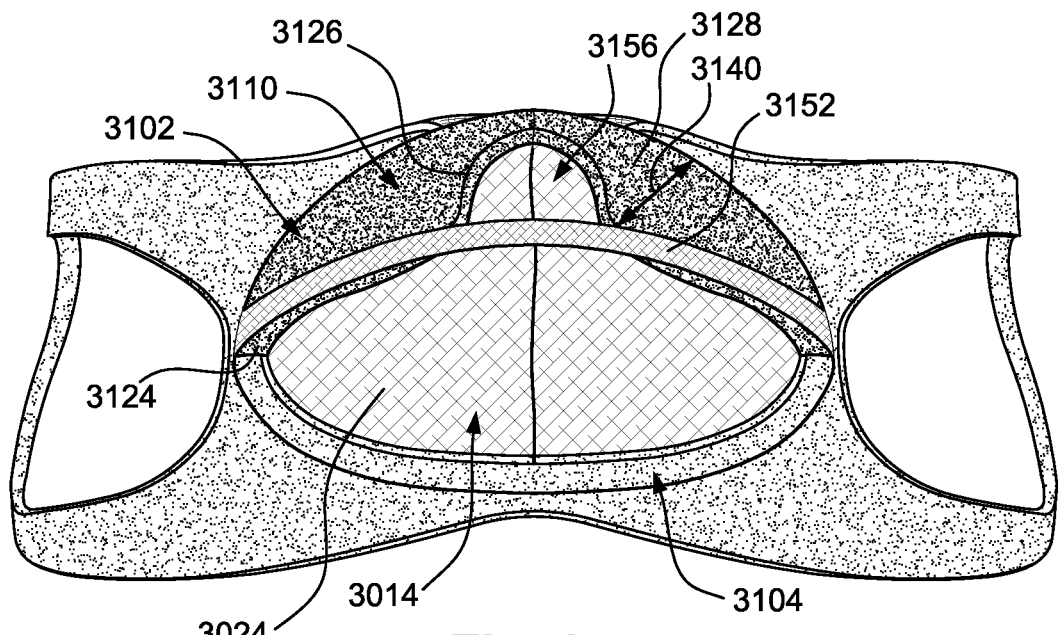

FIG. 15 is a rear view of another form of a hygiene mask, which includes a bridge extending across the seal forming structure.

Figure 16:
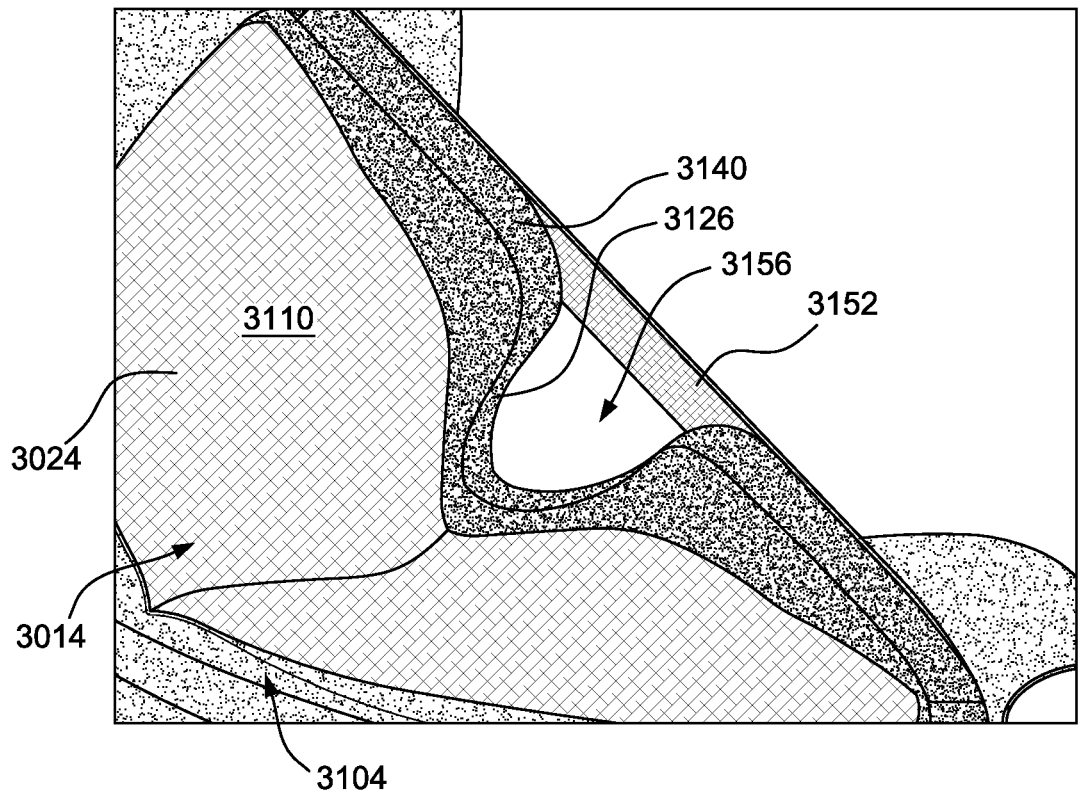

FIG. 16 is a perspective view from behind and below of the hygiene mask of FIG. 15.

BRIEF DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

In the examples illustrated herein the mask 3000 is in the form of a hygiene mask, although the mask illustrated may also be used to filter non-biological particles or pollutants. However, in another form a mask 3000 of the present technology may be used to interface respiratory equipment to its wearer, for example by providing a flow of air to an entrance to the airways. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of between about 6 cmH2O and relative to ambient pressure, for example about 10 cmH2O. In examples configured for use as a hygiene mask, the seal may only be sufficient to seal at normal pressures associated with unassisted inspiration and exhalation. In examples the mask may be configured to allow a small amount of leakage around the user's mouth and a seal may only be formed around the user's nose.

Mask Body

Referring first to FIGS. 4 to 8, some forms of the mask 3000 include a body 3010. The body 3010 may also be referred to as a shell. The body 3010 may include an outer perimeter 3012 with a shape that may substantially correspond to a portion of the user's face. For example, the outer perimeter 3012 may have a substantially reuleaux triangle shape (see e.g., FIG. 5), and may correspond to a perimeter around the user's mouth. More particularly, the outer perimeter 3012 of the body 3010 may extend from the user's lip inferior, radially outside of the user's cheilions, and to the user's pronasale. The user's mouth and nares are positioned radially within the outer perimeter 3012 when the body 3010 is positioned against the user's face in this orientation. In other forms, the outer perimeter 3012 may have a different shape (e.g., circular, elliptical, triangular, rectangular, etc.), and still capture the user's nares and mouth within the outer perimeter 3012. The size and shape of the body 3010 may assist with forming a substantially small footprint of the mask 3000 in order to minimize obstruction to the user's field of view.

In some forms, the body 3010 may include a three-dimensional shape so that a surface of the body 3010 is not in contact with the user's face in use. For example, a central portion of the body 3010 may be out of plane with respect to the outer perimeter 3012 of the body 3010. The body 3010 may include an arcuate or substantially cupped shape (or domed shape), so that the outer perimeter 3012 of the body 3010 lies on a notional hyperbolic paraboloid surface, as best seen in FIG. 10. An inner surface of the body 3010 (e.g., the surface facing the user in use) may include a substantially positive curvature with respect to the user wearing the mask 3000. For example, the inner surface of the body 3010 may form a positive domed shape with respect to the user's face while in use.

The cup shape of the body 3010 may at least partially form a chamber 3014 into which the user breathes, as best seen in FIG. 7. The curved shape of the body 3010 spaces at least a portion of the body 3010 away from the user's face in order to form the volume of the chamber. In use, the user's nose (e.g., the user's nares) and the user's mouth may extend at least partially into the chamber 3014. However, the cupped shape body 3010 limits contact between the user's nares and/or mouth, and the material of the body 3010. This may assist in decreasing a feeling of claustrophobia in a user because the material of the body 3010 is not directly contacting and/or blocking the user's nares and/or mouth, and obstructing the user's breathing. The material of the body 3010 may only contact the user's face laterally outside of the user's cheilions. In some forms, the material of the body 3010 may only contact the user's face at or laterally outside of the nasolabial sulcus on either side of the user's face. In examples where the mask 3000 is a hygiene mask, an internal pressure (e.g., an operating pressure) of the chamber 3014 may be substantially equal to atmospheric pressure, in use. In examples (not shown) where the mask is a patient interface for respiratory pressure therapy, the chamber may be a plenum chamber, which may receive pressurized air to assist in alleviating a breathing disorder (e.g., sleep apnea) in a user.

In certain forms, the body 3010 may be constructed from a semi-rigid or rigid material. The rigidity of the body 3010 may allow the chamber 3014 to maintain its shape (e.g., the cupped shape) regardless of whether the mask 3000 is in use. The material used to construct the body 3010 may assist in maintaining a constant volume of the chamber 3014 when a user is wearing the mask 3000. For example, the semi-rigid or rigid material may not be drawn toward the user's mouth and/or nares when the user inhales. This may limit airway blockages caused by the body 3010 and/or may limit the user's uncomfortableness with wearing the mask 3000 (e.g., thereby promoting increased usage of the mask 3000). This may limit disruptions when the user speaks (e.g., may reduce muffling of the user's speech).

In certain forms, a single piece of material (e.g., semi-rigid or rigid material) may be used to construct the cup-shaped body 3010. A thermoforming process may be used to maintain the shape of the material in the cupped shape (e.g., regardless of whether the mask 3000 is in use).

In certain forms, two or more pieces of material (e.g., semi-rigid or rigid materials) may be used to construct the cup-shaped body 3010. The material may be a spacer material (e.g., an approximately 2-3 mm thick spacer material), although any material with similar properties may be used (e.g., Breath-O-Prene®). For example, the material may be generally soft and compressible in order to provide a comfortable fit to the user. The two or more pieces may be ultrasonically welded together in order to form the cup-shape of the body 3010.

In one form, the two pieces of material are welded together with a curved weld in order to form the curved, cupped-shape of the body 3010. A spine 3034 is formed between the two pieces of material after the weld is complete in the location where the weld occurred. The spine 3034 may add stiffness and/or rigidity to the body 3010. This added stiffness may assist in maintaining the cup-shape of the body 3010 (e.g., when the mask 3000 is tightened against the user's face).

The radius of curvature of the spine 3034 may be inversely related to the stiffness of the body 3010. For example, as the radius of curvature increases (e.g., forms a flatter curve and approaches a planar surface), the stiffness of the body 3010 decrease. Therefore, it may be desirable to form the welded spine 3034 with a smaller radius of curvature in order to increase the stiffness of the body 3010.

However, forming the spine 3034 with a radius of curvature that is too small will create a body 3010 that does not provide adequate space for the user's face. Thus, there is an ideal depth to height ratio range for the body 3010. The two pieces of material may be welded together with a height that is both small enough to provide sufficient stiffness and the large enough to fit the user's facial features. Similarly, the depth is both large enough to fit the user's facial features, and small enough to avoid unnecessarily obstructing the user's field of vision.

In some forms, an additional piece of material with a v-fold 3035 may be connected to the body 3010 (e.g., an outer surface of the body 3010 and/or an inner surface of the body 3010). The v-fold material 3035 may be similar to the material used to construct the body 3010 in that the material is permeable (or porous) and does not obstruct the user's breathing. The v-fold material 3035 may be added in order to cover the spine 3034, and promote the aesthetics of the mask 3000.

In certain forms (see e.g., FIGS. 6 and 10), the material of the body 3010 (e.g., either the single piece of material, or the two or more pieces of material) may include at least one pleat 3022 (e.g., one pleat 3022 on the left side and one pleat on the right side of the body 3010). The pleats 3022 may allow the material of the body 3010 to maintain the cupped, arcuate shape, without wrinkles, or other bends in the material. In other words, the pleats 3022 may provide a substantially smooth surface (e.g., without folds or creases), particularly along the outer perimeter 3012. This may assist in minimizing leakage between the outer perimeter 3012 and the user's face (e g , minimizing inhaled and exhaled air from flowing around the mask 3000 instead of through the body 3010). In some forms, the pleat 3022 may not be necessary when the body 3010 is thermoformed (e.g., when the body 3010 is constructed with a single piece of material). In some forms, the pleat(s) 3022 may be covered by the v-fold material 3035.

In some forms, at least a portion of the body 3010 is configured to allow passage of air into and out of the chamber 3014. In examples where the mask 3000 is configured as a patient interface (e.g., for treating a respiratory disorder), the body 3010 may be provided with one or more ports for connection to an air circuit (e.g., which may provide a flow of pressurized breathable air to the chamber 3014). The body 3010 may optionally be provided with one or more vents through which air may enter and/or exit the chamber 3014.

In examples which are configured for use as a hygiene mask, the body 3010 may comprise a permeable portion through which air can pass. In other words, the user may inhale breathable air from an environment external to the chamber 3014, and may exhale air into the external environment. The material of the body 3010 allows a flow of air between the external environment and the chamber 3014. This helps to reduce the likelihood that the user will continue to inhale previously exhaled air. The body 3010 may be constructed from a permeable material. The body 3010 may be permeable because of material properties (e.g., nylon, cotton, or polyester).

The permeable properties of the material may allow for even airflow across the surface of the body 3010. In some forms, the body 3010 may be shaped (e.g., with the positively domed shape) so that airflow through the permeable material is not directed toward the user's eyes. In other examples, the body 3010 may be altered so that the permeable material may not direct airflow into the user's eyes. For example, the body 3010 may be coated to alter (e.g., reduce) the permeability in certain sections (e.g., proximate to the upper portions of the body 3010). In this way, more airflow (e.g., specifically exhaled air) passes through the body 3010 distal to the user's eyes.

In some forms, the entire body 3010 may be made from a material through which air can pass (e.g., an open cell foam, a textile, etc.). For example, the body 3010 may be constructed from a textile like a spacer fabric. Suitable fabrics are described in PCT Publication WO2013026091, the contents of which is incorporated herein in its entirety. The permeable material of the body 3010 may also be rigid or semi-rigid in order to maintain the cupped shape. As shown in FIG. 4-1, the permeable material may also be rigidized (e.g., via a chemical or mechanical process) in order to increase the rigidity of the permeable material so that it may maintain the substantially cupped shape. The material may be rigidized outwardly from the center of the mask 3000 (e.g., from the spine 3034). For example, the body 3010 may be rigidized along directions radiating outwardly from the center of the mask 3000 (e.g., in a spider web shape). The two-dimensional rigidized pattern 3038 may assist in maintaining the three-dimensional profile (e.g., cupped shape) of the mask 3000. However, the rigidized pattern 3038 may not prevent a user from manually manipulating the body 3010. The rigidized pattern 3038 would be flexible enough to allow a user to stretch or compress the body 3010 when donning or doffing the mask 3000, and would return the body 3010 to its original shape (i.e., the cupped shape) after the user removes the external force. The body 3010 may be selectively rigidized using a process (e.g., electric current, chemical reaction, application of force) described in PCT/SG2020/050792, the entire contents of which is incorporated in its entirety. At least one of the processes described in PCT/SG2020/050792 may be selectively applied to predetermined locations of the body 3010 in order to rigidize the selected locations. The locations may be selected in order to assist in maintaining the three-dimensional shape (e.g., cupped shape) of the body 3010. Alternatively, or in addition, stitching may be added to the body 3010 in a predetermined pattern in order to selectively rigidize the body 3010.

Alternatively, the body 3010 may be permeable because of modifications made during manufacturing. For example, the body 3010 may be constructed from a material with a non-permeable material property. The body 3010 of a mask 3000 (e.g., a hygiene mask) may be provided with one or more ports, passages, apertures and/or vents 3030 as illustrated in FIG. 5-1. The port(s) 3030 (e.g., microscopic or visible) may be added to the material to provide selective permeability. The port(s) 3030 may have a greater permeability than the remainder of the body 3010. The body 3010 may also be substantially impermeable, and fluid flow between the external environment and the chamber 3014 may only be permitted through the port 3030. Such modified non-permeable materials may include, but are not limited to, cellulose acetate, cellulose nitrate (e.g., collodion), polyamide (nylon), polycarbonate, polypropylene, and/or polytetrafluoroethylene (Teflon).

In examples with multiple ports 3030, each port 3030 may be spaced (e.g., approximately evenly spaced) from adjacent ports 3030. The ports 3030 may be located at positions on the body 3010 that are less likely to cause eye irritation of fogging of glasses if worn. For example, the ports 3030 may be located towards the bottom portion of the body 3010 (e.g., along the spine 3034 and proximate to the portion 3132 in order to be positioned in front of the user's mouth). The ports may be located toward the sides of the body 3010 (e.g., proximate to the perimeter 3012 of the body 3010) to direct airflow laterally from the user's face. However, the ports 3030 may not be located toward the top portion of the body 3010 (e.g., proximate to the cantilever portion 3110) to avoid directing air towards the user's eyes. Moreover, the ports 3030 could be located throughout the body 3010 (e.g., top, bottom, middle, and/or sides). The ports 3030 may be structured such that inhaled air can be taken in through all of the ports 3030 (regardless of location, even ports 3030 located on the upper half near the eyes), but only select ones of the ports 3030 allow exhaled gas to pass—e.g., the ports 3030 that are not prone to cause eye jetting/eyeglass fogging. For example, ports 3030 located proximate the upper portion of the body 3010 (e.g., proximate to the cantilever structure 3110), may be structured as a one-way valve, and may only allow inhaled air to enter the chamber 3014, but may prevent exhaled air from leaving the chamber 3014. This can be accomplished via one or more flaps that open on inhalation and close on exhalation. Or may be accomplished by an auxetic material (e.g., a material that expands under application of tension) in certain locations (e.g., upper part of the body 3010 proximate to the cantilever structure 3110) that tends to cause closure of the passages due to forces created during exhalation. In other examples, at least some of the ports 3030 may be tapered so that the smaller diameter opening is inside of the chamber 3014 and the larger diameters are outside of the chamber 3014 on the outer surface of the body 3010. The tapered ports 3030 may allow air to more freely flow in one direction (e.g., inhaled air traveling into the chamber 3014) and more difficultly in the opposite direction (e.g., exhaled air exiting the chamber 3014). This may be useful proximate to the upper portion of the chamber to limit airflow into the user's eyes.

In examples, the mask 3000 is configured such that air which passes through a port, aperture or vent 3030 in the body 3010 also passes through a filter element 3024 (described below). In examples, any and all ports, apertures or vents 3030 provided are located within the perimeter of the seal forming structure 3100. The port, aperture, or vent 3030 may be proximate a central region of the body 3010 and substantially aligned (e.g., on a common horizontal plane perpendicular to the sagittal plane) with the user's mouth and/or nares so that inhaled and/or exhaled air flows directly through the port 3030 and into the user's airways. In other forms, the port, aperture, or vent 3030 may be disposed at any location along the body 3010 (e.g., proximate to the outer perimeter 3012).

In some forms, a deformable object 3028 (e.g., a thin metal strip, a wire, etc.) may be coupled to the body 3010. Specifically, the deformable object 3028 may be coupled to the body 3010 proximate to an edge (e.g., proximate to the outer perimeter 3012). The deformable object 3028 may be deformed by the user to alter the shape of a superior portion 3020 of the body 3010 to better suit the shape of the individual user's nose and face (see e.g., FIGS. 11A and 11B). The deformable object 3028 may be plastically deformable so that it keeps its desired shape (i.e., does not elastically return to different position) after being bent, or otherwise manipulated. The deformable object may act as a rigidizer when connected to the body 3010, and may increase the stiffness of the body 3010.

In some forms, the deformable object 3028 may be positioned proximate to a central superior portion 3016 of the perimeter 3012 of the body 3010 (see e.g., FIG. 8). Specifically, a user may bend or manipulate the deformable object 3028 in order to conform to the contours of their nose (e.g., the lateral curvature of the periphery 1100). In this may, the mask 3000 may substantially avoid contacting the user's nasal ridge. (e.g., the nose seal portion 3102 may contact the user's nose entirely inferior to the user's nasal ridge). Users with smaller (e.g., narrower) noses may manipulate the deformable member 3028 to include a smaller radius of curvature, while users with larger (e.g., wider) noses may manipulate the deformable member 3028 to include a larger radius of curvature. Users may make multiple adjustments (e.g., depending on their particular comfort level or position on the user's bridge). Multiple users may also wear a single mask 3000 (e.g., a mask 3000 may be reusable and washable), and each user may need to adjust the deformable member 3028 to their individual face.

In other forms, the deformable object 3028 may extend around a different portion of the outer perimeter 3012 of the body 3010 (e.g., around the sides and/or around a central inferior portion). In still other examples, the deformable object 3028 may extend around the entire outer perimeter 3012 of the body 3010. The user may be able to adjust different portions of the deformable object 3028 in order to substantially match a variety of portions of their face.

As shown in FIG. 4-2, some forms of the body 3010 may include a three-dimensional rigidizer 3042. The three-dimensional rigidizer 3042 may constructed from the same material as the body 3010 (e.g., a permeable material). The three-dimensional rigidizer 3042 may be used in addition to, or instead of the deformable object 3028 and/or the two-dimensional rigidized pattern 3038. The three-dimensional rigidizer 3042 would be flexible enough to allow a user to stretch or compress the body 3010 when donning or doffing the mask 3000, and would return the body 3010 to its original shape (i.e., the cupped shape) after the user removes the external force.

In some forms, the three-dimensional rigidizers 3042 may be arranged in a similar pattern as the two-dimensional rigidizer pattern 3038 (e.g., in a spider web shape). However, the three-dimensional rigidizers 3042 may be spaced apart from the spine 3034 (e.g., in order to avoid interfering with a filter element 3024, described below). The three-dimensional rigidizers 3042 may extend toward the user's face, although they may be positioned to avoid irritating the user's face. In other forms, the three-dimensional rigidizers 3042 may connected in other patterns (e.g., around at least a portion of the perimeter 3012 of the body 3010). In any pattern, the three-dimensional rigidizers 3042 assist in maintaining the three-dimensional shape of the body 3010 without disturbing the user's comfort.

In some examples, the body 3010 is made of a textile where the outer surface (i.e., the surface exposed to the external environment) has some degree of water repellence. This may be by way of the material property of the textile or by applying a coating to the outer surface. In some forms, the coating may not substantially affect the permeability of the body 3010. In some forms, the coating may make the body 3010 impermeable, and air may enter and/or exit the chamber 3014 through a port, aperture, or vent 3030. In some examples, the coating may also be applied to the inner surface 3032 of the body 3010 (i.e., the surface within the chamber 3014). The water repellent coating may assist in limiting the saturation of the textile material with exhaled water vapor. The coating may be rubber, polyvinyl chloride (PVC), polyurethane (PU), silicone elastomer, fluoropolymers, and/or wax.

Alternatively, a material may be removably coupled to the interior of the body 3010 which has water repellent properties. In other examples, the material may be a medium which can filter particles of certain sizes (e.g., a filter medium 3024, described below). The user may selectively choose whether to use the removable material.

In some forms, the inner surface 3032 of the body 3010 within the chamber 3014 may include at least one fastener 3026 for coupling the removable material to the mask 3000. In some forms, the body 3010 may include a pair of fasteners 3026, one on either lateral side (e.g., left and rights sides) of the body 3010. The fasteners 3026 may be hook and loop material, magnets, mechanical snaps, or any other similar fastening elements that permit removable connections.

As shown in FIG. 8-1, some forms of the inner surface 3032 of the body 3010 may include a pocket 3046. For example, the pocket 3046 may be connected (via stitching, ultrasonic welding, etc.) to the inner surface 3032 around a portion of the perimeter of the pocket 3046. At least one fastener 3026 may be connected to the inner surface 3032 within and/or proximate to the pocket 3046. The pocket 3046 may substantially follow the curvature of the body 3010 to create a substantially small opening to the pocket 3046, and to limit decreasing user comfort.

Spacer Fabric

A spacer fabric can be defined as a textile having an upper ground structure or layer, a lower ground structure or layer, and a floating or traversing yarn woven between the upper ground structure and lower ground structure to form a matrix like textile.

The upper ground structure and lower ground structure may be formed from a fabric. The upper ground structure may have different properties to the lower ground structure, for example they may have different stretch, stiffness, flexibility, hand feel, or other characteristics. The upper and lower ground structures may be substantially parallel to one another. Spacer fabrics may be formed by flat knitting. At least one side (i.e. upper or lower ground structure) may be formed from a fabric having yarn of, for example, about 30-100 denier, 20-300 denier, or 50-200 denier for a pleasant hand feel. This may reduce irritation of the body 3010 when in contact with the user's skin.

Seal Forming Structure

As shown in FIGS. 2-1 and 7 to 8-1, some forms of the present technology may include a seal-forming structure 3100 provides a target seal-forming region, and may additionally provide a cushioning function. The target seal-forming region is a region on the seal-forming structure 3100 where sealing may occur and form a sufficient seal. The region where sealing actually occurs—the actual sealing surface—may change within a given period of use, from day to day, and from user to user, depending on a range of factors including, but not limited to, where the mask was placed on the face, tension in the positioning and stabilising structure, and/or the shape of a user's face. The target seal-forming region may be sufficiently large in order to maintain substantially the same seal with different actual sealing surfaces. In other words, the same user who places the seal-forming structure 3100 in a slightly different location on their face on different days will experience substantially the same seal because the target seal-forming region is large enough to include many actual sealing surfaces.

In examples shown in FIGS. 7 to 8-1, the seal forming structure 3100 may comprise an under nose seal portion 3102 and/or a mouth seal portion 3104. The under the nose seal portion 3102 may substantially extend in a plane 3106 which is different to the plane 3108 of the mouth seal portion 3104. These two seal portions 3102, 3104 may work together to form a seal around substantially the entire outer perimeter 3012 of the seal-forming structure 3100 between the user's face and the mask 3000. For example, the two seal portions 3102, 3104 cooperatively form a single seal against the user's face, which may surround both the user's nares and the user's mouth.

As shown in FIG. 7, the plane 3106 may be inclined with respect to a central axis 3107 (e.g., an axis co-linear with or parallel to the spine 3034, and/or parallel to or coplanar with the sagittal plane, in use) prior to use in some forms. The force from the user's nose may cause an angle between the plane 3106 and the central axis 3107 to further increase. However, the material of the nose seal portion 3102 may have sufficient stiffness to limit substantial increase in the angle. In some forms, the angle 3109 between the plane 3106 and the central axis 3107 prior to use may be between approximately 100° and approximately 170°. In some forms, the angle 3109 between the plane 3106 and the central axis 3107 prior to use may be between approximately 110° and approximately 140°. In some forms, the angle 3109 between the plane 3106 and the central axis 3107 prior to use may be between approximately 115° and approximately 125°. In some forms, the angle 3109 between the plane 3106 and the central axis 3107 prior to use may be approximately 120°.

As shown in FIG. 7, the angle between the plane 3106 and the central axis 3107 may be designed to accommodate users with large angles between their columella and lip superior. In some forms, the angle between the columella and the lip superior may substantially match the angle between the plane 3106 and the central axis 3107. Substantially matching the angle between the plane 3106 and the central axis 3107 with the angle on the user's face promotes effective sealing in users with large angles between the columella and the lip superior. Users with smaller angles between their columella and the lip superior may bend the nose seal portion 3102 with contact between their nose and the mask 3000 and change the angle between the plane 3106 and the central axis 3107 to substantially correspond to their face (e.g., and create a sufficient seal).

Under Nose Seal Portion

As shown in FIGS. 4 and 7, the nose seal portion 3102 of the seal forming structure 3100 is configured to form a seal around a periphery 1100 of the user's nose (e.g. as shown in FIG. 3) and/or around the sides of a portion of the user's nose immediately adjacent the periphery 1100. The periphery 1100 may extend around at least a portion of the user's nares on an inferior side (e.g., lower portion) of the user's nose. The inferior side of the nose may be inferior to the inferior to the user's pronasale and the ridge of the user's nose. Specifically, the periphery 1100 may extend from the user's alar base adjacent to their lip superior and along their nasal ala back to the alar base. The periphery 1100 may extend radially outside of the perimeter both nares (e.g., and does not intersect with the nares and/or extend into either of the nares). The periphery 1100 may also extend up to the user's pronasale. In total, the periphery 1100 may form a substantially C-shape or a substantially U-shape. In other words, the periphery 1100 may not intersect the user's sagittal plane along the user's lip superior (although some forms may include a completely closed periphery).

As shown in FIG. 4, some forms of the nose seal portion 3102 comprises a cantilever structure 3110 which extends from the body 3010 toward a center of the mask 3000 (e.g., radially inwardly from the outer perimeter 3012). The cantilever structure 3110 may be fixed proximate to an outer edge of the body 3010. The free end of the cantilever structure 3110 may be positioned toward the center of the mask 3000. The free end of the cantilever structure 3110 may be able to move into and out of the chamber 3014 depending on a direction of an applied force.

As shown in FIG. 4, certain forms of the mask 3000 may include two cantilever portions 3110. For example, the mask 3000 may include a cantilever portion on either side (i.e., a right side and a left side) of the mask 3000. Each cantilever portion 3110 may be symmetrical about the central axis 3107 of the mask 3000. The cantilever portions 3110 may be joined together proximate to the central axis 3107 of the mask 3000 (e.g., at a location intended to contact the user's nose proximate to the user's pronasale). An exposed surface of the seam between the cantilever portions 3110 may be substantially smooth in order to reduce irritation with the user's skin. Any raised or projecting portion may be disposed on the opposite surface of the cantilever portions 3110 within the chamber 3014 so as to avoid contact with the user's skin.

As shown in FIG. 8, certain forms of the cantilever portion 3110 may avoid obstructing the fasteners 3026. In other words, the cantilever portion 3110 may not extend over the fasteners 3026, so that the fasteners 3026 are visible. This may assist the user in aligning a filter element 3024 (described below) with the fasteners 3026.

As shown in FIG. 7, the cantilever portion 3110 may include an anterior edge 3120 and a posterior edge 3126. The anterior edge 3120 may be substantially linear and may extend the entire length of the cantilever portion 3110. The posterior edge 3126 of the cantilever portion 3110 may be at least partially arcuate. For example, the cantilever portion 3110 may be curved from a central portion 3122 toward a maximum width 3140. Specifically, the posterior edge 3126 may have a positive curvature with respect to the user's nose, in use. In some forms, the radius of curvature at the maximum width 3140 may be between approximately 10 mm and approximately 50 mm. In some forms, the radius of curvature at the maximum width 3140 may be between approximately 20 mm and approximately 40 mm. In some forms, the radius of curvature at the maximum width 3140 may be between approximately 25 mm and approximately 35 mm. In some forms, the radius of curvature at the maximum width 3140 may be approximately 30 mm.

The maximum width 3140 may be the length of a chord extending from the posterior edge 3126 and perpendicular to the anterior edge 3120. In some forms, the measured maximum width 3140 is less than twice the radius of curvature (e.g., a partial diameter) because the anterior edge 3120 is substantially linear. For example, the measured maximum width 3140 may be between approximately 25% and approximately 95% of twice the radius of curvature. For example, the measured maximum width 3140 may be between approximately 40% and approximately 80% of twice the radius of curvature. For example, the measured maximum width 3140 may be between approximately 50% and approximately 70% of twice the radius of curvature. For example, the measured maximum width 3140 may be approximately 66% of twice the radius of curvature.

In some forms, the measured maximum width 3140 may be between approximately 1 mm and approximately 50 mm. In some forms, the measured maximum width 3140 may be between approximately 10 mm and approximately 40 mm. In some forms, the measured maximum width 3140 may be between approximately 15 mm and approximately 30 mm. In some forms, the measured maximum width 3140 may be approximately 20 mm.

As shown in FIGS. 4 to 4-2, some forms of the cantilever portion 3110 may be a middle portion between the central portion 3122 and the lateral portion 3124. However, the cantilever portion 3110 may be non-symmetrical on either side of the maximum width 3140 between the central portion 3122 and the lateral portion 3124. For example, the maximum width 3140 may not be cantilever portion 3110 may be off center. In some forms, the maximum width 3140 may be closer to the lateral portion 3124, which may create a larger space between the two maximum widths 3140 (e.g., on either side of the central portion 3122), which may provide a larger space for the user's nose. In other forms, the maximum width 3140 may be evenly spaced between the central portion 3122 and the lateral portion 3124, or the maximum width 3140 may be disposed closer to the central portion 3124.

In some forms, the shape of the cantilever portion 3110 may be non-uniform on either side of the maximum width 3140. For example, the cantilever portion 3110 may be substantially linear between the maximum width 3140 and the lateral portion 3124 (e.g., the length being tangent to the radius at the maximum width 3140). This distance may be inclined with respect to the anterior edge 3120. In some forms, the length may include a curvature proximate to the lateral portion 3124. This may provide a substantially smooth transition between the anterior and posterior edges 3120, 3126 in order to limit irritation with the user's skin. In some forms, the radius of curvature at the maximum width 3140 may be between approximately 10 mm and approximately 50 mm. In some forms, the radius of curvature at the maximum width 3140 may be between approximately 20 mm and approximately 40 mm. In some forms, the radius of curvature at the maximum width 3140 may be between approximately 25 mm and approximately 35 mm. In some forms, the radius of curvature at the maximum width 3140 may be approximately 30 mm.

In certain forms (see e.g., FIGS. 4 and 7), the width between the anterior and posterior edges 3120, 3126 at the lateral edge 3124 may be substantially negligible. In other words, the curvature proximate to the lateral edge 3124 may merge the posterior edge 3126 into the anterior edge 3120 so that there is substantially no thickness between the edges 3120, 3126.

With continued reference to FIGS. 4 and 7, some forms of the cantilever portion 3110 may be symmetrical about the central portion 3122 regardless of whether the cantilever portion 3110 is constructed from a single piece of material or from separate pieces of material. In a single-piece construction, the central portion 3122 is not an edge, and only marks an axis of symmetry. In a multi-piece construction, the central portion 3122 is an edge on either cantilever portion 3110 prior to joining the cantilever portions 3110.

In some forms, a length between the central portion 3122 and a lateral edge may be between approximately 50 mm and approximately 150 mm. In some forms, a length between the central portion 3122 and a lateral edge may be between approximately 75 mm and approximately 125 mm. In some forms, a length between the central portion 3122 and a lateral edge may be between approximately 80 mm and approximately 100 mm. In some forms, a length between the central portion 3122 and a lateral edge may be approximately 89 mm. In some forms, the length may be adjusted on different sized mask 3000 in order to conform to different sized faces. For example, some forms of the length may be no more approximately 15 mm less (e.g., approximately 74 mm). As described below, this reduced length may still provide sufficient facial contact to form a hygiene mask quality seal.

In some forms, the cantilever portion 3110 is coupled to the body 3010 with an adhesive (e.g., glue). For example, an adhesive may be applied along the anterior edge 3120 and/or the inner surface 3032 proximate to the outer perimeter 3012. The adhesive may form a substantially air-tight interface between the cantilever portion 3110 and the body 3010 in order to limit leaks. The adhesive may also serve to increase the stiffness of the mask 3000 (e.g., the adhesive may act as a rigidizer). In other examples, the cantilever portion 3110 and the body 3010 may be connected to one another using a different method (e.g., ultrasonic welding, mechanical couplings, magnets, etc.). These other methods of connection may also act as rigidizers for the mask 3000. In still other examples, the cantilever portion 3110 and the body 3010 may be constructed from the same piece of material in a one-piece and/or integral connection. Once the cantilever portion 3110 is connected to the body 3010, the posterior edge 3126 may be disposed closer to the user's face (e.g., positioned further rearward) than the anterior edge 3120 in use.

As best seen in FIGS. 4 and 7, the anterior edge 3120 of the cantilever structure 3110 is curved out of plane to match the perimeter 3012 of the body 3010. In other words, the compliant nature of the material used in the cantilever structure 3110 allows the anterior edge 3120 to bend and match the shape of the body 3010 along the outer perimeter 3012. The cantilever portion 3110 may curve about an axis directed into the user's face in use (e.g., about an axis parallel to or co-planar with the sagittal plane, or an axis inclined with respect to the sagittal plane). In some forms, a central portion 3122 of the anterior edge 3120 of the cantilever structure 3110 is superior to the lateral portions 3124 of the anterior edge 3120 of the cantilever structure 3110 as a result of the curvature. In some forms, the central portion 3122 may be more anterior than the lateral portions 3124 as a result of the curvature (e.g., because the user's pronasale may be the anterior-most facial feature). Because the cantilever structure 3110 is curved, portions of the posterior edge 3126 (i.e., the free end) may be configured to move into the chamber 3014 in different directions. For example, FIG. 7 illustrates that the portion of the posterior edge 3126 proximate to the central portion 3122 is oriented in a substantially horizontal direction (e.g., in a substantially lateral direction intersecting the user's sagittal plane), and the posterior edge 3126 proximate to the lateral portions 3124 is oriented in a substantially vertical direction (e.g., in a substantially superior-inferior direction in use). In some forms, the cantilever portion 3110 may be curved on either side of the central portion about the maximum width 3140. In other words, the arcuate portion adjacent to the maximum width 3140 may be a transition between the substantially horizontal portion and the substantially vertical portion.

The posterior edge 3126 proximate to the central portion 3122 may be movable into the chamber 3014 in the inferior direction, and the posterior edge 3126 proximate to lateral portions 3124 may be movable into the chamber 3014 in the anterior direction. The curvature of the cantilever structure 3110 may stiffen the cantilever structure 3110 such that it is better able to resist bending in an inferior direction (e.g. when deflected downward by the underside of the user's nose) than would be the case if the entire cantilever structure 3110 was substantially planar when connected to the body 3010.

The cantilever structure 3110 is configured to engage the inferior periphery 1100 of the user's nose without occluding the user's nares, or at least without significantly or without totally occluding the nares (see e.g., FIG. 3-1). In other words, the portion of the cantilever portion 3110 between the two maximum widths 3140 may include a curvature (e.g., a C-shape or a U-shape) as a result of being connected to the body 3010. The shape may substantially conform to the shape of the periphery 1100 of the user's nose. Specifically, the posterior edge 3126 of the cantilever structure 3110 may be shaped to substantially conform to the shape of an outer edge of the inferior surface of a typical user's nose (e.g., along the user's alar rims). Additionally, the maximum widths 3140 may be configured to contact the user's face proximate to the alar base. The curvature at the maximum widths 3140 may provide a comfortable interface against the user's skin. The maximum widths 3140 may extend across the corners of the user's nose proximate to the alar base along a sealing perimeter 1105. In some forms, the cantilever structure 3110 proximate to the maximum width 3140 may be wedged into the corner region of the user's nose proximate to the alar base. The wedged material may assist in providing an effective seal and reducing the likelihood of leak in that region. As shown in FIG. 3-1, some forms of the cantilever structure 3110 may not extend around the entire periphery 1100, and may diverge from the user's nose proximate to the corner region in order to bridge the space between the periphery 1100 and the user's cheek.

As shown in FIG. 2-1, the nasal seal 3102 may contact the user's face between the nasal ala and the nasolabial sulcus in order to bridge the corner of the user's nose. The specific cantilever shape and maximum width portion 3140 may assist in wedging into the corner region and forming an effective seal. As described, the seal may then contact the user's face outside the corner of the mouth and around the mouth and along to total sealing perimeter 1105.

As described above, in some examples the shape of the posterior edge 3126 may be varied (e.g. made narrower or wider) by bending a deformable object 3028 in the body 3010. For example, FIG. 11A illustrates the deformable element 3028 is set for a wider and/or shorter nose, and FIG. 11B illustrates the deformable element is set for a narrower and/or longer nose. The deformable element 3028 allows the user to adjust the shape of the nose seal portion 3102 to better conform to their face.

As shown in FIG. 9, the cantilever structure 3110 may be configured to seal against both sides of the inferior periphery 1100 of the user's nose from a point immediately inferior to the tip of the nose to points where the nose meets the face, directly inferior to the alar crest. The cantilever structure 3110 contacts and/or seals against the user's nose slightly inferior to the user's pronasale so that the pronasale is not positioned within the chamber, in use. However, the cantilever structure 3110 may not extend superior to the user's pronasale (e.g., may not contact the ridge of the user's nose). In some forms, the cantilever structure 3110 may not extend above the tip of the user's nose.

In use, the user's nose may press downward (i.e. in an inferior direction) on a superior surface 3128 of the cantilever structure 3110 adjacent the posterior edge 3126 of the cantilever structure 3110, thereby causing the cantilever structure 3110 to bend downward (i.e. in an inferior direction). The cantilever structure 3110 may exert an opposing force on the underside of the user's nose, thereby sealing against the inferior periphery of the user's nose. This may provide the cantilever structure 3110 some resistance so that the user's nose does not sink entirely into the chamber 3014 and a good seal is established between the nose seal portion 3102 and the user's face.

As shown in FIGS. 15 and 16, some forms of the mask 3000 may include a bridge 3152 for providing additional support to a user's nose and providing additional resistance so that the user's nose does not sink entirely into the chamber 3014 and a good seal is established between the nose seal portion 3102 and the user's face.

As shown in FIG. 15, the bridge 3152 extends across the cantilever structure 3110. The bridge 3152 may be connected to a portion of the cantilever structure 3110. For example, the bridge 3152 may overlay the cantilever structure 3110, and may be bonded (e.g., connected via an adhesive) to the cantilever structure 3110. The bridge 3152 may be substantially thin (e.g., as compared to the thickness of the cantilever portion 3110). The substantially small thickness of the bridge 3152 may maintain a substantially smooth and/or flush superior surface 3128 of the cantilever portion 3110. For example, the bridge 3152 may not noticeably protrude from the superior surface 3128 to limit creating a ridge or corner that could cause the user irritation. This may assist in providing a comfortable surface (e.g., superior surface 3128) for the user.

In some forms, the bridge 3152 may extend between locations proximate to the lateral portions 3124. The bridge 3152 may also intersect the posterior edge 3126 proximate to the maximum width 3140 on either side of the cantilever structure 3110. This may create a substantially curved path that the bridge 3152 follows. As shown in FIG. 16, a central portion of the bridge 3152 may extend between the posterior edge 3126 (or posterior edges 3126) between the maximum widths 3140, and may be unsupported (i.e., may not overlay the cantilever portion 3110). In some forms, the bridge 3152 may be connected in a substantially taut orientation across the unsupported region.

In certain forms, the bridge 3152 is formed from a piece of material that is between approximately 1 mm and approximately 15 mm wide (e.g., as measured in the anterior-posterior direction). In certain forms, the bridge 3152 is formed from a piece of material that is between approximately 5 mm and approximately 10 mm wide. In certain forms, the bridge 3152 is formed from a piece of material that is approximately 7 mm wide.

In certain forms, the bridge 3152 is formed from a piece of material with a length that is approximately 10 mm and approximately 50 mm long (e.g., measured between the maximum widths 3140 of the posterior edge 3126 (or posterior edges 3126)). In certain forms, the bridge 3152 is formed from a piece of material with a length that is approximately 20 mm and approximately 40 mm long. In certain forms, the bridge 3152 is formed from a piece of material with a length that is approximately 35 mm long.

With the addition of the bridge 3152, the mask 3000 may contact a complete perimeter around the user's nose. For example, the cantilever structure 3110 contacts the periphery 1100 as described in the previous example. The inclusion of the bridge 3152 forms a completed perimeter that receives the user's nares. In other words, the bridge 3152 contacts the user's face between the alar bases and across the lip superior. The bridge 3152 may contact the user's subnasale, and the user's nares may extend into and partially through the space created by the cantilever structure 3110 and the bridge 3152.

The bridge 3152 may be able to deform when in contact with the user's lip superior. The bridge 3152 may be constructed from a flexible material and is unsupported, allowing the flex when a force is applied. In some forms, the bridge 3152 may be constructed from an elastic material. The elastic material may assist the bridge 3152 in stretching, which may assist in promoting comfort in the user. For example, the elasticity in the bridge 3152 may provide give and limit the stiffness of the material contacting the lip superior and/or pronasale (e.g., which may be sensitive regions). The bridge 3152 may elastically deform and return to its initial taut position after each use.

In certain forms, a position of the cantilever structure 3110 is movable by bending the deformable member 3028. As the deformable member 3028 is moved into a wider orientation, the elastic material of the bridge 3152 is stretched and remains in a taut position. Moving the deformable member 3028 does not move the bridge 3152 into a plastic deformation region, which allows the bridge 3152 to stretch further when in contact with the user and return to its original taut position when the deformable member 3028 is moved into a narrower orientation. As the deformable member is moved into the narrower orientation, the elastic material remains in a taut position so that a user with a narrower nose may retain the benefit of the elastically deformable bridge 3152.

In some forms, the bridge 3152 may assist the user with properly orienting the mask 3000 on their face. For example, the bridge 3152 may limit the user from positioning the cantilever structure 3110 superior to the pronasale and in contact with the nasal ridge. The material of the bridge 3152 and the opening 3156 created by the cantilever structure 3110 and the bridge 3152 encourages the user to properly orient their nose within the mask 3000. The opening 3156 is sized to approximately correspond to the size of a user's nose, so that the user is encouraged to properly position their nose within the mask 3000. As described above, the deformable object 3028 may be adjusted in order to change the size of the opening 3156 and accommodate different sized noses while still limiting the improper positioning of a user's nose.

In some forms, the bridge 3152 may limit the user's nose from extending completely into the chamber 3014. The bridge 3152 may provide a reaction force as a result of contact with the user's nose. In other words, the tension in the bridge 3152 limits the length extension of the bridge 3152. Thus, the bridge 3152 may assist in properly orienting the user's nose in the superior-inferior direction. The tension in the bridge 3152 may prevent the user's nose from extending too deep into the chamber 3014 (e.g., where the nasal bridge is at least partially within the chamber 3014). The nose may then contact the cantilever portion in the desired location and form a seal.

The cantilever structure 3110 may be constructed from foam, for example, closed cell foam (e.g., Belmont foam). The foam may be substantially air-tight. In other words, the foam may have a substantially low permeability as compared to the material of the body 3010 so that air travels through the body 3010 and not through the cantilever structure 3110. Alternatively, the foam may be entirely impermeable. For example, the foam may be thicker than the material of the body 3010 (e.g., a textile), which may contribute to the reduced permeability. In some forms, the foam may be between approximately 1 mm thick and approximately 20 mm thick. In some forms, the foam may be between approximately 2 mm thick and approximately 15 mm thick. In some forms, the foam may be between approximately 4 mm thick and approximately 10 mm thick. In some forms, the foam may be between approximately 6 mm thick and approximately 10 mm thick. In some forms, the foam may be approximately 8 mm thick.

In examples, the cantilever structure 3110 may be semi-permeable foam or may include holes (e.g., similar to ports 3030) which may be substantially evenly spaced. The any holes may be located to direct airflow away from the user's face in order to reduce causing eye irritation or fogging of glasses if worn. For example, holes in the cantilever structure 3110 may be disposed proximate to the lateral portions 3124 to direct airflow laterally from the user's face, and to avoid directing air towards the user's eyes. In some examples, the cantilever structure 3110 may be structured such that inhaled air can be taken in through the material, but only selected locations (or no locations) allow exhaled gas to pass—e.g., to avoid causing eye jetting/eyeglass fogging. For example, the cantilever structure 3110 may be structured as or to include a one-way valve, and may only allow inhaled air to enter the chamber 3014, but may prevent exhaled air from leaving the chamber 3014 (exhaled air may exit through the body 3010 as described above). This can be accomplished via one or more flaps that open on inhalation and close (the hole(s)) on exhalation. Another alternative may include an auxetic material in certain locations (e.g., proximate to the lateral portions 3124) that tends to cause closure of the passages due to slightly higher forces created during exhalation. In other examples, at least some holes in the cantilever structure 3110 may be tapered so that the smaller diameter opening is inside of the chamber 3014 and the larger diameters are outside of the chamber 3014 (e.g., on the superior surface 3128) on the outer surface of the body 3010. The tapered ports 3030 may allow air to more freely flow in one direction (e.g., inhaled air traveling into the chamber 3014) and more difficultly in the opposite direction (e.g., exhaled air exiting the chamber 3014). This may be useful proximate to the upper portion of the chamber to limit airflow into the user's eyes.

The foam may expand in a direction perpendicular to the applied force, which may cause the foam to partially or completely cover the user's nares. To limit this, the foam may not be overly compressible (e.g., because of material properties and/or because of thickness). This may assist in limiting the occurrence of occluded nares. Even when not substantially compressible, the foam may be comfortable for the user. In some forms, the foam used to construct the cantilever structure 3110 may be generally stretchy. However, the thickness of the cantilever structure 3110 generally limits the total length extension (e.g., in order to limit the occurrence of occlusion). The cantilever structure 3110 may still be stretchier than the body 3010, which is intended to maintain the cupped shape.

In certain forms, the superior surface 3128 of the cantilever structure 3110 may be coated (e.g., silicone coated) in order to increase impermeability. The coating may be substantially smooth and provide a comfortable feel to the user. In other forms, the superior surface 3128 may remain uncoated, which may limit the cantilever structure 3110 from sticking to the user's face (e.g., and creating creases and folds where leaks could occur).

Of course, the cantilever structure 3110 may be constructed from other materials such as textiles. A cantilever structure 3110 constructed from another material may have a similar thickness to the cantilever structure 3110 constructed from the foam. For example, the cantilever portion 3110 may be constructed from a substantially impermeable textile, vinyl, silicone, thermoplastic polyurethane. These other materials may also have limited compressibility in order to limit occluding the user's nares in use. These materials may also have limited stickiness or tackiness in order to avoid sticking to the user's face.

As shown in FIGS. 7 to 8-1, some forms of the foam (or other material used to construct the cantilever portion 3110) may include substantially the same thickness along its entire length (e.g., from lateral portion 3124 to lateral portion 3124, or from lateral portion 3124 to central portion 3122). In other forms, the foam (or other material) used to construct the cantilever structure 3110 may include a varying thickness. The thickness may vary between the lateral portion 3124 and the central portion 3122 and/or between the anterior edge 3120 and the posterior edge 3126.

In certain forms, the foam may be thickest between the central and lateral portions 3122, 3124 (e.g., a thickest portion may be proximate the maximum width 3140 and the thinnest portions may be proximate to the central and lateral portions 3122, 3124). The increased thickness of the foam proximate to the maximum widths 3140 may assist the foam conforming to the sharp corners of the user's face, and ensuring material of the cantilever portion 3110 completely fills the user's alar base region, which may limit leaks. The thinner region proximate to the central portion 3122 and/or the lateral portions 3124 may reduce irritation against more sensitive portions of the user's skin. In other forms, the varying thicknesses may be reversed (i.e., so that the maximum width 3140 is thinner than the central portion 3122 and/or the lateral portion 3124.

In certain forms, the foam may be thicker proximate to the anterior edge 3120 and thinner proximate to the posterior edge 3126. The thinner material proximate to the user's nares maybe more comfortable. However, other forms may have the thicker portion proximate to the posterior side 3126, which may provide a better seal.

In use, the cantilever portion 3110 contacts an inferior surface of the user's nose around the periphery 1100. As shown in FIGS. 9 and 9-1, the alar rims of the user's nose may contact the cantilever portion 3110 between the central portion 3122 and the respective lateral portion 3124. The user's nose may apply a contact force to the cantilever portion 3110, which may bend the cantilever portion 3110 in the inferior direction. For example, the cantilever portion 3110 may bend into the cavity 3014 as a result of contact with the user's nose. The resilient properties of the material used in constructing the cantilever portion 3110 may resist the contact force from the user's nose. This may establish the necessary seal against the user's nose. The seal between the cantilever portion 3110 and the user's face limits air in the chamber 3014 from leaking around the outer perimeter 3012. The combination of the low permeability of the cantilever portion 3110 and the seal between the user's face and the cantilever portion 3110 may direct the airflow through the body 3010. In some forms, between approximately 50% to approximately 100% of inhaled and exhaled airflow passes through the body 3010. In some forms, between approximately 75% to approximately 100% of inhaled and exhaled airflow passes through the body 3010. In some forms, between approximately 90% to approximately 100% of inhaled and exhaled airflow passes through the body 3010. In some forms, approximately 95% of inhaled and exhaled airflow passes through the body 3010. In some forms, approximately 100% of inhaled and exhaled airflow passes through the body 3010. In other words, inhaled and exhaled air may flow along the path of least resistance. Because the body 3010 includes a lower permeability and the body 3010 is not sealed against the user's face, airflow is able to enter and exit the chamber along the anterior-posterior direction, and is limited from traveling in the superior-inferior direction (e.g., through the cantilever portion 3110).

Limiting airflow in the superior-inferior direction may assist in maintaining the airflow away from the user's eyes. Directing exhaled air in the anterior, and not superior direction, may particularly assist in reducing the irritation of the user. The temperature of the exhaled air may be higher than the inhaled air as a result of heat transfer that occurs within the user's airways. This warm, exhaled air may condense on solid surfaces in cooler air temperatures (e.g., if the air temperature of the user's environment is less than the temperature of the exhaled air). This can be particularly irritating to a user who wears glasses (e.g., the exhaled air may condense on the surface of the glasses, which may be cooler than the temperature of the exhaled air). This may limit a user's vision. Even if a user does not wear glasses, the warm exhaled air may dry out the user's eyes and cause irritation. Directing the airflow away from the user's eyes limits the occurrence of this issue.

Even if some air did pass through the cantilever portion 3110, or between the cantilever portion 3110 and the user's face, the airflow may not be directed toward the user's eyes. The central portion 3122 contacts the user's nose proximate to, or adjacent to, the user's pronasale. But the central portion 3122 does not extend superior to the tip of the user's nose, and does not extend along the bridge of the user's nose. Thus, a direction superior to the cantilever portion 3110 is at least partially in front of the user's eyes (e.g., the airflow may pass in the superior direction without going into the user's eyes). Additionally, by not extending along the user's nasal ridge (e.g., avoiding any contact with the user's nasal ridge), the cantilever portion 3110 does not act to direct air (e.g., exhaled air) along the user's nasal ridge in the posterior direction.

In other forms, the cantilever portion 3110 includes the highest impedance, while the rest of the mask 3000 (e.g., the body 3010 and the mouth seal portion 3104) includes a lower impedance. These lower impedances can be equal or can be different (e.g., the impedance of the mouth seal portion 3104 may be between the impedances of the cantilever portion 3110 and the body 3010). Airflow can pass through the path of least resistance, and is more likely to pass through the body 3010 and/or the mouth seal portion 3104 as opposed to the cantilever portion 3110. In this way, airflow (e.g., particularly warm exhaled air) is less likely to flow toward the user's eyes, and will instead flow in the anterior and inferior directions away from the user's face.

In other forms, the cantilever portion 3110 may be at least partially permeable (e.g., less permeable than the inner surface 3032 of the body 3010). Airflow (e.g., exhaled air) may pass through the cantilever portion 3110, but the reduced permeability of the cantilever portion 3110 (e.g., as compared to the body 3010) may assist in diffusing the air. For example, the entire stream of exhaled air passing through the cantilever portion 3110 may not be directed in a common direction (e.g., toward the user's eyes). This may also assist with promoting user comfort (e.g., by limiting irritation in and/or around the user's eyes).

Mouth Seal Portion

As shown in FIGS. 4 and 8, some forms of the mask 3000 may include the mouth seal portion 3104 which extends from the nose seal portion 3102, around the sides of the user's mouth and below the user's mouth. Together, the nose seal portion 3102 and the mouth seal portion 3104 may form a substantially complete seal around the outer perimeter 3012 of the body 3010.

In some forms, portions 3130 of the mouth seal portion 3104 are formed by the cantilever structure 3110 (e.g. by a portion of the posterior edge 3126 of the cantilever structure 3110 between the maximum width 3140 and the lateral portion 3124). The portions 3130 of the cantilever structure 3110 which seal around the user's mouth may extend from an area directly inferior to the user's nose to the sides of mouth area, as seen in FIG. 9. For example, the portions 3130 of the cantilever structure 3110 may extend from a region of the user's face proximate to the alar base toward the nasolabial sulcus. In some forms, the portions 3130 may not extend below the user's lip superior in use. In examples, the seal forming structure 3100 does not seal against the region above the lip superior directly inferior to the user's subnasale and nares. In this way, the user is not prevented from breathing through their nose into the chamber.

In some forms, the mouth seal portion 3104 comprises a portion 3132 configured to seal around a lower portion of the user's face. For example, the portion 3132 may seal between the chin and the lip inferior, and may extend between the lateral portions 3124 of the cantilever structure 3110. This may make the mask 3000 appear less bulky compared to masks which extend below the user's chin because the mouth seal portion 3104 has a smaller footprint on the user's face.

In some forms, the portion 3132 may be constructed from a single piece of material. The portion 3132 may be connected to the outer perimeter 3012 of the body 3010 in a similar manner as the cantilever structure 3110 (e.g., via gluing, ultrasonic welding, mechanical fasteners, magnets, etc.). Once connected to the body 3010, the portion 3132 may include an arcuate shape (e.g., a semi-elliptical shape) that will contact the user's face from one nasolabial sulcus, laterally outside the user's mouth to the lip inferior, and to the opposite nasolabial sulcus. In other forms, the portion 3132 may be constructed from two pieces of material. The two portions may be joined at approximately a center axis of the body 3010 (e.g., substantially in line in the inferior-superior direction with the central portion 3122).

In some forms (see e.g., FIGS. 11A and 11B), the portion 3132 may not extend from the body 3010 in a cantilevered manner In other words, the portion 3132 may not extend into the chamber 3014. Instead, the portion 3132 may extend substantially perpendicularly from the body 3010 (e.g., toward the user's face, in use). Contact with the user's face may compress the portion 3132 (e.g., in the anterior direction) into the body 3010.

As shown in FIG. 8, some forms of the portion 3132 may be structured as a flange 3134 which extends from the periphery of the body 3010. Additionally, or alternatively, if the body 3010 is made from a suitable material (e.g. a suitable textile or foam) a portion of the mouth seal portion 3104 may comprise a periphery of the body 3010.

In some forms, the thickness of the portion 3132 (e.g., measured in the direction generally perpendicular to the body) may be substantially small so that the mask 3000 does not extend a significant distance from the user's face and obstruct the user's line of sight. In some forms, the thickness of the portion 3132 may be between approximately 1 mm and approximately 50 mm. In some forms, the thickness of the portion 3132 may be between approximately 2 mm and approximately 40 mm. In some forms, the thickness of the portion 3132 may be between approximately 3 mm and approximately 30 mm. In some forms, the thickness of the portion 3132 may be between approximately 4 mm and approximately 20 mm. In some forms, the thickness of the portion 3132 may be between approximately 5 mm and approximately 10 mm.

As shown in FIGS. 4 and 8, some forms of the nose seal portion 3102 may merge or blend into the mouth seal portion 3104. In other words, the cantilever structure 3110 may blend into the portion 3132 so that the two sections of the seal-forming structure 3110, 3132 are connected across a substantially smooth transition.

As described above, the cantilever structure 3110 may be connected to the body 3010 along the anterior edge 3120. Specifically, the anterior edge 3120 may be in direct contact with the body 3010 (e.g., proximate to the outer perimeter 3012. As shown in FIG. 8, the cantilever structure 3110 may extend both over the chamber 3014 and may extend in the posterior direction during use.

As shown in FIGS. 4 and 8, the cantilever structure 3110 decreases in width proximate to the lateral portions 3124. In other words, the distance between the posterior edge 3126 and the anterior edge 3120 decreases. Thus, the posterior edge 3126 may merge toward the anterior edge 3120. As the width between the anterior and posterior edges 3120, 3126 decrease, the width of the cantilever portion 3110 becomes closer to the portion 3132. In other words, the lateral portions 3124 have substantially the same thickness as the portion 3132. The cantilever portion 3110 may smoothly transition into the portion 3132. For example, there is a non-discontinuous transition (e.g., not stepped) between the lateral portions 3124 and the portions 3132. This may be helped by the curved shape of the lateral portions 3124, which allow for the smooth transition.

As shown in FIG. 8, some forms of the mask 3000 may include an angle between the portion 3132 and the cantilever structure 3110. While the interface between the portion 3132 and the cantilever structure 3110 may be smooth (e.g., with minimal or no sharp corners), the interface may not be entirely rounded. The angle between the proximate ends of the portion 3132 and the cantilever structure 3110 may be an obtuse angle measured between the posterior edge 3126 and the flange 3134. The angle 3150 between the portion 3132 and the cantilever structure 3110 may correspond to an angle of a user's face proximate to the nasolabial sulcus. In some forms, this angle 3150 may be between approximately 91° and approximately 179°. In some forms, this angle 3150 may be between approximately 110° and approximately 175°. In some forms, this angle 3150 may be between approximately 130° and approximately 170°. In some forms, this angle 3150 may be between approximately 155° and approximately 165°. In some forms, this angle 3150 may be approximately 165°. The angle 3150 may approach 180°, as the facial topography proximate to the user's nasolabial sulcus may approach vertical in some users. The mask may be adjusted (e.g., by bending) in order to provide some adjustment for different users, so that a single mask may fit a wide range of users. Alternatively, multiple sized masks 3000 may be manufactured, with different angles in the above ranges included on each sized mask 3000.

The portion 3132 and the cantilever structure 3110 may be coupled to the body 3010 adjacent to one another so that there is substantially no gap between the portion 3132 and the lateral portions 3124. In some forms, the lateral portions 3124 may be coupled directly to the portion 3132, which may reduce the leaking from the chamber 3014. The portion 3132 and the cantilever structure 3110 may be coupled together in an end-to-end configuration to form a substantially sealed interface (e.g., hygiene mask quality sealed interface). However, so examples may include a small gap (e.g., less than approximately 5 mm) between proximate ends of the portion 3132 and the cantilever structure 3110. In some forms, a shorter cantilever structure 3110 (e.g., shortened by no more than approximately 15 mm) may be used with an accompanying longer portion 3132 (e.g., longer by no more than approximately 15 mm). The shorter cantilever structure 3110 may still press against the cheek region for a hygiene mask quality seal.

In certain forms, the cantilever portion 3110 and the portion 3132 may be constructed from substantially the same material. This may improve user comfort because the user may not perceive a noticeable difference between the portions 3110, 3132.

In certain forms, the cantilever portion 3110 and the portion 3132 may be constructed from the same piece of material so that the cantilever portion 3110 and the portion 3132 are a one-piece construction.

In certain forms, the portion 3132 may be coupled to the body 3010 in a one-piece and/or integral construction. The cantilever portion 3110 may be coupled to the portion 3132 and/or the body 3010 in a one-piece and/or integral construction.

In some forms where the mask 3000 is used with a patient interface for treating a breathing disorder (e.g., using CPAP therapy to treat sleep disorder breathing), the mouth seal portion 3104 may not be included. For example, although some forms of a patient interface may include a full-face seal (i.e., a nose seal portion 3102 and a mouth seal portion 3104), some forms of the patient interface may just include a nose seal portion 3102, and may only seal around the user's nares. For example, the nose seal portion 3102 may seal against the alar rims and the lip superior, and may not contact the lip inferior. In this form, the user's mouth would not be exposed to pressurized air, and would instead remain in an ambient environment.

Filter Element

As noted above, some forms of the body 3010 may comprise a permeable portion through which air can pass. In some forms, the permeable portion may serve to filter the air passing through the permeable portion to a sufficient degree so that no additional filtration (e.g., by a specific filter element) is required. However, in examples where the mask 3000 is configured as a multi-use hygiene mask and/or where a greater degree of filtration is required than would be provided by the material of the permeable portion alone, the mask 3000 may be provided with an additional filter element 3024 (see e.g., FIGS. 13 to 14-2). The filter element 3024 may have a lower permeability than the body 3010 of the mask 3000 so that fewer particles or debris may enter the chamber 3014 and be inhaled by the user and/or so that fewer particles may exit the chamber 3014 after the user exhales. The lower permeability may not substantially affect airflow into and/or out of the chamber (i.e., the filter element 3024 may not negatively affect the user's breathing).

In some forms, the filter element 3024 may be configured to be attached to the fasteners 3026 on the inner surface 3032 within the chamber 3014. As noted above, the fasteners 3026 may be hook and loop fasteners or any other suitable fastener. The filter element 3024 may have corresponding fasteners (not shown) that removably engage with the fasteners 3026. In other forms, the filter element 3024 may be coupled to an outer surface of the body 3010 (e.g., positioned outside of the cavity 3014).

As shown in FIG. 13-1, some forms of the filter element 3024 may be positionable within the pocket 3046. The pocket 3046 may be sized to snuggly receive the filter element 3024. In some forms, the pocket 3046 may include an elastic portion to help retain the filter element. In some forms, the pocket 3046 alone may be sufficient to retain the filter element 3024 during use. However, as shown in FIG. 13-2, fasteners 3026 may be used with the pocket 3046 to provide additional retention.

In either case, the connected filter element 3024 may provide additional stiffness to the mask 3000. In other words, the filter element 3024 may provide additional stiffness to the body and act as an additional rigidizer in order to assist in maintaining the three-dimensional shape (e.g., cupped shape) of the body 3010.

In some forms, the filter element 3024 may be reusable, and may be disconnected from the body 3010 (e.g., after each use) and cleaned, before being reattached to the fasteners 3026.

In other forms, the filter elements 3024 may be disposable, and may be discarded after each use. The user may attach a new, clean filter element 3024 prior to each use.

In some forms, the filter element 3024 may be shaped to substantially correspond to the shape of the body 3010 (see e.g., FIG. 13). For example, the shape of the filter element 3024 may substantially correspond to the shape of the outer perimeter 3012. The filter element 3024 may be positioned against the inner surface 3032 of the body 3010 so that it is at least partially covered by the cantilever element 3110. In other words, a user may position the filter element 3024 underneath the cantilever structure 3110 so that the filter element 3024 may extend to the outer perimeter 3012, and may not interfere with the seal between the user's face and the cantilever structure 3110. The filter element 3024 may be constructed from a substantially flexible material so that a user may bend or otherwise reposition the filter element 3024 so that it fits around the cantilever structure 3110. The rigidity of the body 3010 may assist in maintaining a spacing between the filter element 3024 and the user's airways in order to reduce breathing resistance experienced by the user.

In certain forms like FIG. 15, the filter element 3024 may sit flush against the inner surface 3032 when connected to the fasteners 3026. Thus, the filter element 3024 may not substantially take up the volume of the chamber 3014, and the user's skin may avoid contact with the filter element 3024 in use.

In certain forms, the filter element 3024 may be more rigid around an outer perimeter than proximate to the center. For example, FIGS. 14-1 and 14-2 illustrate a rigid member 3025 that may be coupled to the outer perimeter of the filter element 3024, which may assist the filter element 3024 in maintaining its shape. Although more rigid than the center of the filter element 3024, the rigid member 3025 may be malleable so that a user can adjust the shape of the filter element 3024. For example, the user may adjust the shape of the body 3010 and the cantilever portion 3110 as shown in FIGS. 11A and 11B. The user may also adjust the shape of the filter element 3024 so that it continues to fit flush against the modified shape of body 3010 and/or cantilever portion 3110.

In one form, the rigid member 3025 may be resilient, and may be able to return to a neutral portion when an external force is no longer applied. For example, the user may be able to bend the filter member 3024 in order to fit within the chamber 3014 (see e.g., FIG. 14-1). After the filter member 3024 is positioned in the desired orientation, the rigid member 3025 may return toward its neutral position (see e.g., FIG. 14-2). In other words, the filter member 3024 may expand toward the outer perimeter 3012 of the body 3010. The filter member 3024 may substantially or completely cover the inner surface 3032 of the body 3010 and may limit airflow from passing around the outer edges of the filter member 3024 (e.g., and not being filtered).

In examples where the body 3010 is provided with ports (see e.g., FIG. 5-1), apertures or vents 3030, the filter element 3024 may be configured to extend only across or within the ports, apertures or vents. Fasteners may be disposed proximate to the port, aperture, or vent 3030 so that the filter element 3024 may be positioned directly covering the port, aperture, or vent 3030. In other examples the filter element 3024 may be configured to cover the entire interior surface of the body 3010.

In one example, the filter element comprises material which is substantially the same as that used for prior art surgical masks.

In addition to collecting debris, germs, and/or other particles that a user does not want to inhale, or does not want others to inhale, the filter element 3024 may block spittle from contacting the body 3010. The filter element 3024 may protect the body 3010 and keep the body 3010 relatively clean. This may allow a user to change only the filter element 3024 and to continue to use the body 3010 for multiple uses without washing.

In some forms, the filter element 3024 may include an electric charge to assist in trapping debris. For example, the debris may have a negative charge. The filter element may have a positive charge in order to attract the negatively charged debris. Alternatively, the filter element 3024 may have a negative charge in order to attract positively charged debris.

Positioning and Stabilising Structure

As shown in FIGS. 7, 8, and 12, the mask 3000 is provided with a positioning and stabilising structure or headgear 3300 that assists in maintaining the in use position of the body 3010 and seal-forming structure 3100 against the user's face. The positioning and stabilising structure 3300 may provide a force (e.g., a sealing force) directed at least partially in the posterior direction in order to provide sufficient contact and seal force between the seal-forming structure 3100 and the user's skin.

As shown in FIG. 12, some forms of the headgear 3300 is formed as headgear and includes loops 3302 which loop around the user's ears and hold the mask 3000 in position. Each loop 3302 may form a complete perimeter (i.e., no interruptions or breaks in the material). This may assist in limiting the loops 3302 from becoming tangled. The loops 3302 may be made from a suitably elastic textile or foam (e.g., an elastic foam). This may allow the loops 3302 to expand and stretch when the user dons and/or doffs the mask 3000 in order to fit around different sized ears. This may also allow the loops 3302 to return to a relaxed state while the mask 3000 is in use so that the loops 3302 contact the user's ear and provide the sealing force.

As shown in FIG. 12, some forms of the loops 3302 may contact the user's face while engaged to the user's ears. For example, each loop 3302 may rest against the respective user's cheek inferior to the user's eyes (e.g., the loops do not significantly protrude from the user's cheek and may be considered substantially flush with the user's face). The material of the loops 3302 may be substantially thin in order to avoid obstructing the user's line of sight. The thin material may also make stretching the loops 3302 easier because the thinner material has less resistance to stretching.

In certain forms, the loops 3302 may be the stretchiest portion of the mask 3000. In other words, the loops 3302 may extend the greatest length of any portion of the mask 3000 under tension. The stretchiness help to maximize the fit range of the mask 3000 (i.e., increases the different sized heads that can wear the same sized mask 3000). The thickness of each loop 3302 may be minimized in order to provide maximum stretchiness, while providing sufficient strength (e.g., so that the loop 3302 does not break upon application of tension).

In some forms, each loop 3302 may be constructed from a foam material with a thickness between approximately 0.1 mm and approximately 10 mm. In some forms, each loop 3302 may be constructed from a foam material with a thickness between approximately 1 mm and approximately 5 mm. In some forms, each loop 3302 may be constructed from a foam material with a thickness between approximately 1.5 mm and approximately 4 mm. In some forms, each loop 3302 may be constructed from a foam material with a thickness of approximately 2 mm.

In some forms, each loop 3302 may be constructed from a textile (e.g., a braided textile) material with a thickness between approximately 0.1 mm and approximately 10 mm. In some forms, each loop 3302 may be constructed from a textile (e.g., a braided textile) material with a thickness between approximately 0.5 mm and approximately 5 mm. In some forms, each loop 3302 may be constructed from a textile (e.g., a braided textile) material with a thickness between approximately 0.75 mm and approximately 4 mm. In some forms, each loop 3302 may be constructed from a textile (e.g., a braided textile) material with a thickness of approximately 1 mm.

As shown in FIGS. 5-6 and 12, some forms of the loops 3302 may include an elongated and/or substantially elliptical shape. For example, a superior and inferior side of each loop 3302 may be substantially parallel to one another. A distance between an upper edge of the superior side and a lower edge of the inferior side is approximately equal to the height of the body 3010. In other words, the footprint of the loops 3302 in the inferior-superior direction may be substantially the same as the footprint of the body 3010 in the same direction.

As shown in FIGS. 5 to 5-2, some forms of the loops 3302 are configured to connect to, or engage, substantially the entire perimeter 3012 of the body 3010, or at least a majority of the perimeter 3012 of the body 3010, rather than attaching to the body 3010 at narrower, or more localised, points. The positioning of the loops 3302 may assist in reducing or eliminating creasing of the body 3010, in particular at portions of the body 3010 which form part of the seal forming structure 3100.

In some forms, the headgear 3300 attaches to the inside periphery 3136 of the inferior half of the body 3010 and thereby forms at least a part of the mouth seal portion 3104 of the seal forming structure 3100. In examples the headgear 3300 is attached to the body by an adhesive (e.g., gluing, taping, or a combination of gluing and taping), ultrasonic welding, sewing, mechanical fasteners, or any similar means of attachment. The adhesive may also serve to increase the stiffness of the mask 3000 (e.g., the adhesive may act as a rigidizer). In other forms, the headgear 3300 may be connected to the body 3010 with a one-piece and/or integral connection (e.g., constructed from the same sheet of material so that an attachment means is unnecessary).

In some forms, the headgear 3300 may be coupled to the body 3010 proximate to the anterior edge 3120 and the superior surface 3128. As shown in FIGS. 7 and 12, the headgear 3300 may include a superior arm 3306 and an inferior arm 3308 on either lateral side of the mask 3000. Each superior arm 3306 may be connected to a superior portion of the body 3010 (e.g., proximate to the cantilever portion 3110), and each inferior arm 3308 may be connected to an inferior portion of the body 3010 (e.g., proximate to the portion 3132). The superior and inferior arms 3306, 3308 on either lateral side (e.g., left and right) may be formed as a single piece of material and may merge together in order to form the loop described above.

As shown in FIGS. 9 and 9-1, some forms of the superior arm 3306 may be connected to an edge 3036 of the body 3010. The edge 3036 may form the outer boundary of the outer perimeter 3012. The edge 3036 may also be oriented substantially perpendicularly to the inner surface 3032. Thus, the superior arm 3306 may be oriented proximate to the superior surface 3128 of the cantilever portion 3110. An adhesive (e.g., gluing, taping, or a combination of gluing and taping), ultrasonic welding, sewing, mechanical fasteners, or any similar means of attachment may be applied to each superior arm 3306 and/or to the edge 3036. Any of these means of attachment also serve to increase the stiffness of the mask 3000 (e.g., the adhesive may act as a rigidizer).

With continued reference to FIGS. 9 and 9-1, some forms of each superior arm 3306 may extend in a substantially parallel direction to at least a section of the cantilever portion 3110 (e.g., proximate to the maximum width 3140). In some forms, each superior arm 3306 may be substantially tangential to a section of the cantilever portion 3110 (e.g., tangential to the central portion 3122). In some forms, the superior arms 3306 may be spaced apart from one another (e.g., not connected at the central portion 3122).

In some forms, the upper edge 3310 of each superior arm 3306 may be substantially linear. As shown in FIG. 7, the width of each superior arm 3306 may decrease toward the central portion 3122 so that each superior arm 3306 may merge into the body 3010 (e.g., the edge 3036). The upper edge 3310 of each superior arm 3306 may be substantially co-linear with the edge 3036. Thus, the superior arms 3306 may not significantly add to the footprint of the mask 3000. The linear shape of the upper edges 3310 may also assist in directing the sealing force up and into the user's face.

In certain forms (see FIG. 6), the superior arm 3306 and/or the inferior arm 3308 may taper along their length. For example, the superior arm 3306 and/or the inferior arm 3308 may be wider proximate to the body 3010 and may decrease in width distal to the body 3010. The wider portion near the body 3010 may assist in forming a better connection between the body 3010 and the arms 3306, 3308 (e.g., greater surface area to connect to) and/or increased stability between the body 3010 and the arms 3306, 3308. The narrower portions of the arms 3306, 3308 may assist in increasing user comfort. For example, thinner arms 3306, 3308 results in less surface area to contact the user, which can decrease sources of irritation. Additionally, the narrowest portion of the arms 3306, 3308 may extend around the user's ear in use. This may assist in providing a force to the posterior portion of the user's ear that is less likely to cause irritation.

As shown in FIG. 7, the inferior arms 3308 may connect to the body in a similar manner as the superior arms 3306. For example, the inferior arms 3308 may also connect (via an adhesive, ultrasonic welding, sewing, mechanical fasteners, or any similar means of attachment) to the edge 3036. The inferior arms 3308 may be connected to the edge 3036 in a substantially perpendicular orientation to the portion 3132 coupled to the inner surface 3032. Any of these means of attachment also serve to increase the stiffness of the mask 3000 (e.g., the adhesive may act as a rigidizer).

As shown in FIG. 8, some forms of ends of the inferior arms 3308 may be connected to the body 3010 in close proximity to one another. For example, the ends of the inferior arms 3308 may touch one another.

With continued reference to FIG. 8, some forms of the inferior arms 3308 may include a slight bend 3312. In other words, the lower edge 3314 of each inferior arm 3308 may not be entirely linear (e.g., instead including two inclined sections). The bend 3312 may orient the lower edge 3314 so that it is substantially parallel with the upper edge 3310 and the superior and inferior arms 3306, 3308 direct the sealing force in substantially the same direction.

In one form, the loops 3302 may be provided with sliding adjusters (not shown) to allow the effective size of the loops to be adjusted. This may allow the loops 3302 to be made from a less elastic material. Instead, the user may move the adjuster away from the body 3010 (e.g., toward a free end of each loop 3302) so that the loops is larger than their ear in order to don and/or doff the loops 3302. The user then may move the adjuster toward the body 3010 (e.g., toward the end fixed to the body 3010) in order to adjust the size of the loops 3302 so that they provide a sufficient sealing force and sufficient comfort.

In one form, the headgear 3300 may include a pair of upper straps and a pair of lower straps. The upper straps and the lower straps are all connected to the body 3010. However, each upper straps is not joined with the respective lower strap to form a loop. In other words, the respective upper and lower straps do not have an unbroken piece of material. Instead, users may tie the straps together to form a loop. The user may form a knot a selected length in order to change the size of the loop. The upper straps may also be tied together and the lower straps may be tied together. In other words, the connected upper straps may contact a posterior portion of the user's head overlaying the parietal bone, and the connected lower straps may contact the posterior portion of the user's head overlaying the occipital bone.

In other forms of the technology, for example if the mask 3000 is configured for use as a CPAP patient interface, alternative forms of positioning and stabilising structure may be used, for example headgear comprising one or more straps which extend around the patient's head. Conduits to convey air into the chamber 3014 may also serve as straps.

Glossary

General

Air: In certain forms of the present technology, air may be taken to mean atmospheric air, and in other forms of the present technology air may be taken to mean some other combination of breathable gases, e.g. oxygen enriched air.

Leak: The word leak will be taken to be an unintended flow of air. In one example, leak may occur as the result of an incomplete seal between a mask and a user's face. In another example leak may occur in a swivel elbow to the ambient.

Materials

Fiber: A filament (mono or poly), a strand, a yarn, a thread or twine that is significantly longer than it is wide. A fiber may include animal-based material such as wool or silk, plant-based material such as linen and cotton, and synthetic material such as polyester and rayon. A fiber may specifically refer to a material that can be interwoven and/or interlaced (e.g., in a network) with other fibers of the same or different material.

Textile: A material including at least one natural or artificial fiber. In this specification, a textile may refer to any material that is formed as a network of interwoven and/or interlaced fibers. A type of textile may include a fabric, which is constructed by interlacing the fibers using specific techniques. These include weaving, knitting, crocheting, knotting, tatting, tufting, or braiding. Cloth may be used synonymously with fabric, although may specifically refer to a processed piece of fabric. Other types of textiles may be constructed using bonding (chemical, mechanical, heat, etc.), felting, or other nonwoven processes. Textiles created through one of these processes are fabric-like, and may be considered synonymous with fabric for the purposes of this application.

Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

Anatomy

Anatomy of the Face

Ala: the external outer wall or "wing" of each nostril (plural: alar).

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius): A point on the face between the mouth and supramenton, lying in the median sagittal plane.

Lip, upper (labrale superius): A point on the face between the mouth and nose, lying in the median sagittal plane.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion.

Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

User Interface

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a user interface in position on a user's face (e.g., for delivery of respiratory therapy). Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Tie (noun): A structure designed to resist tension.

Vent (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

Curvature in One Dimension

The curvature of a plane curve may be described as having a sign (e.g. positive, negative) and a magnitude (e.g. 1/ radius of a circle that just touches the curve).

Positive curvature: If the curve turns towards the outward normal, the curvature at that point will be taken to be positive (if the imaginary small person leaves the point they must walk uphill). Such curves are often referred to as concave.

Zero curvature: If the curve is a straight line, the curvature will be taken to be zero (if the imaginary small person leaves the point, they can walk on a level, neither up nor down).

Negative curvature: If the curve turns away from the outward normal, the curvature in that direction at that point will be taken to be negative (if the imaginary small person leaves the point they must walk downhill) Such curves are often referred to as convex.

Curvature in Two Dimensions

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small.

Principal curvatures and directions: The directions of the normal planes where the curvature of the curve takes its maximum and minimum values are called the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.).

Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means +/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior technology. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A mask for use at an operating pressure substantially equal to atmospheric pressure, the mask comprising:
    a body forming a three-dimensional shaped chamber configured to operate at the operating pressure throughout a user's respiratory cycle and configured to receive the user's mouth and nares, wherein an inner surface of the body is configured to be spaced apart from the user in use throughout the user's respiratory cycle; and
    a nose portion having a surface defining a plane at its most superior side that is configured and sized to avoid contact with and intersection of the user's nasal ridge, the surface on the most superior side of the nose portion being configured to contact the user's nose along the user's sagittal plane and around at least a portion of the user's nares on an inferior side of the user's nose inferior to the user's nasal ridge without intersecting the user's sagittal plane at the user's lip superior and without entering the user's nasal passages, at least a portion of the nose portion is configured to direct airflow through the user's nose and is configured to limit airflow toward the user's eyes in use; and
    a positioning and stabilising structure to provide a force to hold the nose portion in position on the user's head;
    wherein at least a portion of the body is configured to allow passage of air into and out of the three-dimensional shaped chamber.

2. The mask of claim 1, wherein at least a portion of the body is permeable, such that the body is configured to allow air to enter and exit the three-dimensional shaped chamber through a surface of the body in front of the user's mouth.

3. The mask of claim 1, wherein the body comprises a port through which air can enter and exit the three-dimensional shaped chamber, and wherein the body is substantially impermeable and air can only enter and exit the three-dimensional shaped chamber through the port, in use.

4. The mask of claim 1, wherein the nose portion includes a cantilever structure configured to extend from the body towards the user's face in use, the cantilever structure configured to extend around anterior and lateral portions of a periphery of an alar base of the user's nose.

5. The mask of claim 4, wherein the cantilever structure includes:
    a central portion configured to contact an inferior region of the user's nose proximate to the user's pronasale;
    a pair of lateral end portions configured to contact the user proximate a nasolabial sulcus; and
    a pair of middle portions, each middle portion of the pair of middle portions located between the central portion and one lateral end portion of the pair of lateral end portions, each middle portion configured to contact the user's face proximate to the alar base.

6. The mask of claim 5, further comprising a bridge connected to the nose portion, and wherein the bridge extends between each middle portion.

7. The mask of claim 4, wherein the cantilever structure includes a pair of ends configured to extend partially around the user's mouth.

8. The mask of claim 1, wherein the body is formed from a spacer fabric, a foam, and/or a thermoformed material.

9. The mask of claim 1, wherein the body is formed from a rigid or semi-rigid material, and wherein the body maintains its three-dimensional shape configured to space an interior surface of the body away from the user's lips in use.

10. The mask of claim 1, wherein a central superior portion of a perimeter of the body is provided with a plastically deformable element that is configured to bend and change a shape of the body.

11. The mask of claim 1, further comprising at least one filter element configured to filter air prior to entering and/or exiting the three-dimensional shaped chamber, and wherein the at least one filter element is provided to an interior surface of the three-dimensional shaped chamber.

12. The mask of claim 11, wherein a rigid member is coupled to at least a portion of an outer perimeter of the filter element, the rigid member is resilient and configured to return to a neutral position after a compressive force is removed.

13. The mask of claim 1, wherein the positioning and stabilising structure comprises two elastic loops, each elastic loop configured to engage one of the user's ears.

14. The mask of claim 13, wherein the two elastic loops are connected to the body around at least a majority of a perimeter of the body.

15. The mask of claim 13, wherein the two elastic loops each form a complete, unbroken perimeter.

16. The mask of claim 13, wherein the two elastic loops are thicker proximate to the body, and taper toward a free end distal to the body.

17. The mask of claim 1, further comprising a mouth portion configured to extend around the user's mouth between the user's chin and the user's lip inferior, the mouth portion connected to the nose portion to form a single, continuous structure.

18. The mask of claim 1, wherein the nose portion includes a U-shape and/or a C-shape that is configured to avoid contact with the user's subnasale.

19. The mask of claim 1, wherein the nose portion includes the surface and a lateral edge oriented approximately orthogonal with respect to the surface, the lateral edge and the surface configured to simultaneously contact the user in use.

20. The mask of claim 1, wherein the nose portion is directly connected to the inner surface, and wherein the positioning and stabilising structure is directly connected to an edge of the body oriented substantially perpendicularly with respect to the inner surface.

21. The mask of claim 1, wherein the nose portion is constructed from an at least partially impermeable material.

22. The mask of claim 1, wherein said portion of the nose portion comprises a material that is at least partially permeable and/or comprises a hole configured to direct airflow through material of the nose portion.

23. The mask of claim 22, wherein said portion of the nose portion includes the material that is at least partially permeable, the material being configured to direct airflow in at least two directions.

24. The mask of claim 22, wherein said portion of the nose portion includes said hole, the hole including a valve.

25. The mask of claim 22, wherein said portion of the nose portion includes said hole, the hole including a first opening with a first diameter and a second opening with a second diameter different from the first diameter.

26. The mask of claim 1, wherein the nose portion has a permeability less than a permeability of the body.

27. A mask for use at an operating pressure substantially equal to atmospheric pressure, the mask comprising:
a body forming a three-dimensional shaped chamber configured to operate at the operating pressure throughout a user's respiratory cycle and configured to receive the user's mouth and nares, wherein an inner surface of the body is configured to be spaced apart from the user in use throughout the user's respiratory cycle; and
a nose portion having a surface defining a plane at its most superior side configured and sized to avoid contact with and intersection of the user's nasal ridge, the surface being configured to contact the user's nose along the user's sagittal plane and around at least a portion of the user's nares on an inferior side of the user's nose inferior to the user's nasal ridge without intersecting the user's sagittal plane at the user's lip superior and without entering the user's nasal passages, at least a portion of the nose portion is configured to direct airflow through the user's nose and is configured to limit airflow toward the user's eyes in use; and
a positioning and stabilising structure to provide a force to hold the nose portion in position on the user's head;
wherein at least a portion of the body is configured to allow passage of air into and out of the three-dimensional shaped chamber.

* * * * *